(12) United States Patent
Gibson et al.

(10) Patent No.: US 10,307,942 B2
(45) Date of Patent: Jun. 4, 2019

(54) METHOD FOR MAKING AN APERTURED WEB

(71) Applicant: The Procter & Gamble Company, Cincinnati, OH (US)

(72) Inventors: Fredrick William Gibson, Cincinnati, OH (US); Kelyn Anne Arora, Cincinnati, OH (US); John Lee Hammons, Hamilton, OH (US); Norman Scott Broyles, Hamilton, OH (US); Jill Marlene Orr, Liberty Township, OH (US); Timothy Ian Mullane, Union, KY (US); Jody Lynn Hoying, Maineville, OH (US); Karen Denise McAffry, Cincinnati, OH (US); Hugh Joseph O'Donnell, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/944,979

(22) Filed: Apr. 4, 2018

(65) Prior Publication Data
US 2018/0222092 A1  Aug. 9, 2018

Related U.S. Application Data

(63) Continuation of application No. 15/376,825, filed on Dec. 13, 2016, now Pat. No. 9,962,867, which is a
(Continued)

(51) Int. Cl.
*B26F 1/24* (2006.01)
*B26D 1/00* (2006.01)
(Continued)

(52) U.S. Cl.
CPC ........ *B29C 43/46* (2013.01); *A61F 13/15707* (2013.01); *A61F 13/15731* (2013.01);
(Continued)

(58) Field of Classification Search
None
See application file for complete search history.

(56) References Cited

U.S. PATENT DOCUMENTS

| 2,068,456 A | 1/1937 | Hooper |
| 2,275,425 A | 3/1942 | Grabec |

(Continued)

FOREIGN PATENT DOCUMENTS

| EP | 0523683 A1 | 1/1993 |
| EP | 0509012 B1 | 7/1995 |

(Continued)

OTHER PUBLICATIONS

11240 Search Report and Written Opinion for PCT/US2010/022790 dated May 26, 2010.
(Continued)

*Primary Examiner* — Benjamin A Schiffman
(74) *Attorney, Agent, or Firm* — George H. Leal

(57) ABSTRACT

A method for making apertures in a precursor web using a forming apparatus is described herein. The precursor web comprises a film layer and a nonwoven layer having molecular orientation and the forming apparatus comprises an arrangement of teeth. The forming apparatus heats and stretches the precursor web forming apertures therein.

16 Claims, 20 Drawing Sheets

Related U.S. Application Data continuation of application No. 13/290,242, filed on Nov. 7, 2011, now Pat. No. 9,550,309, which is a continuation of application No. 12/366,825, filed on Feb. 6, 2009, now Pat. No. 8,158,043.

(51) Int. Cl.

| | | |
|---|---|---|
| *B26F 1/20* | (2006.01) | |
| *A61F 13/15* | (2006.01) | |
| *B29C 43/22* | (2006.01) | |
| *B29C 43/46* | (2006.01) | |
| *B29C 43/56* | (2006.01) | |
| *B29C 55/08* | (2006.01) | |
| *B29L 31/48* | (2006.01) | |

(52) U.S. Cl.
CPC ......... *A61F 13/15804* (2013.01); *B26F 1/20* (2013.01); *B26F 1/24* (2013.01); *B29C 43/22* (2013.01); *B29C 43/56* (2013.01); *B29C 55/08* (2013.01); *B26D 2001/006* (2013.01); *B29C 2043/464* (2013.01); *B29C 2043/561* (2013.01); *B29C 2043/567* (2013.01); *B29K 2995/0092* (2013.01); *B29L 2031/4878* (2013.01)

(56) References Cited

U.S. PATENT DOCUMENTS

| | | |
|---|---|---|
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |
| 3,073,304 A | 1/1963 | Schaar |
| 3,081,500 A | 3/1963 | Girswold et al. |
| 3,081,512 A | 3/1963 | Griswold |
| 3,137,893 A | 6/1964 | Gelpke |
| 3,355,974 A | 12/1967 | Carmichael |
| 3,496,259 A | 2/1970 | Guenther |
| 3,511,740 A | 5/1970 | Sanders |
| 3,542,634 A | 11/1970 | Such et al. |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,695,270 A | 10/1972 | Dostal |
| 3,718,059 A | 2/1973 | Clayton |
| 3,719,736 A | 3/1973 | Woodruff |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 4,035,881 A | 7/1977 | Zocher |
| 4,042,453 A | 8/1977 | Conway et al. |
| 4,116,892 A | 9/1978 | Schwarz |
| 4,135,021 A | 1/1979 | Patchell et al. |
| 4,276,336 A | 6/1981 | Sabee |
| 4,379,799 A | 4/1983 | Holmes et al. |
| 4,397,644 A | 8/1983 | Matthews et al. |
| 4,465,726 A | 8/1984 | Holmes et al. |
| 4,469,734 A | 9/1984 | Minto et al. |
| 4,588,630 A | 5/1986 | Shimalla |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer et al. |
| 5,144,730 A | 9/1992 | Dilo |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,382,245 A | 1/1995 | Thompson et al. |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,508,080 A | 4/1996 | Sorimachi et al. |
| 5,518,801 A | 5/1996 | Chappell et al. |
| 5,533,991 A | 7/1996 | Kirby et al. |
| 5,554,145 A | 9/1996 | Roe et al. |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Bergman et al. |
| 5,626,571 A | 5/1997 | Young et al. |
| 5,628,097 A | 5/1997 | Benson et al. |
| 5,648,142 A | 7/1997 | Phillips |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro et al. |
| 5,704,101 A | 1/1998 | Majors et al. |
| 5,709,829 A | 1/1998 | Giacometti |
| 5,714,107 A | 2/1998 | Levy et al. |
| 5,723,087 A | 3/1998 | Chappell et al. |
| 5,743,776 A | 4/1998 | Igaue et al. |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,935,682 A | 8/1999 | Wallstrom |
| 5,961,505 A | 10/1999 | Coe et al. |
| 5,964,742 A | 10/1999 | McCormack et al. |
| 5,968,029 A | 10/1999 | Chappell et al. |
| 5,986,167 A | 11/1999 | Arteman et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 | 5/2002 | Dobrin et al. |
| 6,395,122 B1 | 5/2002 | Hisanaka et al. |
| 6,395,211 B1 | 5/2002 | Dettmer et al. |

(56) References Cited

U.S. PATENT DOCUMENTS

| | | |
|---|---|---|
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell et al. |
| D466,702 S | 12/2002 | Carlson et al. |
| 6,506,329 B1 | 1/2003 | Curro et al. |
| 6,537,936 B1 | 3/2003 | Busam et al. |
| 6,620,485 B1 | 9/2003 | Benson et al. |
| 6,632,504 B1 | 10/2003 | Gillespie et al. |
| 6,635,334 B1 | 10/2003 | Jackson et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,739,024 B1 | 5/2004 | Wagner |
| 6,794,626 B2 | 9/2004 | Kiermeier et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,855,220 B2 | 2/2005 | Wildeman |
| 6,863,960 B2 | 3/2005 | Curro et al. |
| 6,872,274 B2 | 3/2005 | Kauschke et al. |
| 6,884,494 B1 | 4/2005 | Curro et al. |
| 7,005,558 B1 | 2/2006 | Johansson et al. |
| 7,037,569 B2 | 5/2006 | Curro et al. |
| 7,410,683 B2 | 8/2008 | Curro et al. |
| 8,158,043 B2 | 4/2012 | Gibson et al. |
| 9,550,309 B2 | 1/2017 | Gibson et al. |
| 2002/0039867 A1 | 4/2002 | Curro et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0191442 A1 | 10/2003 | Bewick-Sonntag et al. |
| 2003/0191443 A1 | 10/2003 | Taylor et al. |
| 2004/0121686 A1 | 6/2004 | Wong et al. |
| 2004/0122396 A1 | 6/2004 | Maldonado et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0229008 A1 | 11/2004 | Hoying |
| 2004/0242097 A1 | 12/2004 | Hasenoehrl et al. |
| 2004/0265533 A1 | 12/2004 | Hoying et al. |
| 2005/0064136 A1 | 3/2005 | Turner et al. |
| 2005/0096614 A1 | 5/2005 | Perez et al. |
| 2005/0123726 A1 | 6/2005 | Broering et al. |
| 2005/0283129 A1 | 12/2005 | Hammons et al. |
| 2006/0019056 A1 | 1/2006 | Turner et al. |
| 2006/0087053 A1 | 4/2006 | O'Donnell et al. |
| 2006/0286343 A1 | 12/2006 | Curro et al. |
| 2012/0049404 A1 | 3/2012 | Gibson et al. |

FOREIGN PATENT DOCUMENTS

| | | |
|---|---|---|
| EP | 0955159 A1 | 11/1999 |
| EP | 0963747 A1 | 12/1999 |
| EP | 1004412 A1 | 5/2000 |
| FR | 2360400 | 3/1978 |
| JP | H012523944 A | 10/1989 |
| JP | H03111198 A | 5/1991 |
| JP | H08260329 A | 10/1996 |
| JP | H0948057 A | 2/1997 |
| JP | 2001105504 A1 | 4/2001 |
| JP | 2002102285 A | 4/2002 |
| JP | 2006149457 A | 6/2006 |
| WO | WO9515138 A1 | 6/1995 |
| WO | WO2001045613 A1 | 6/2001 |
| WO | WO2002100632 A1 | 12/2002 |
| WO | WO2005011936 A1 | 2/2005 |

OTHER PUBLICATIONS

All Office Actions for U.S. Appl. No. 12/366,825 filed Feb. 6, 2009.
All Office Actions for U.S. Appl. No. 13/290,242 filed Nov. 7, 2011.
All Office Actions for U.S. Appl. No. 15/376,825 filed Dec. 13, 2016.

METHOD FOR MAKING AN APERTURED WEB

FIELD OF THE INVENTION

The present invention relates to methods for making apertured webs. Specifically, the method can be used to make three-dimensional apertured films, nonwovens, and laminates thereof with apertures having minimal aspect ratios.

BACKGROUND OF THE INVENTION

Apertured webs are utilized in a wide variety of industrial and consumer products. For example, apertured films or apertured nonwovens are known for use in disposable absorbent articles such as disposable diapers and feminine hygiene articles such as sanitary napkins, and the like. Such articles typically have a fluid pervious topsheet, a fluid impervious breathable backsheet, and an absorbent core disposed between the topsheet and the backsheet. An apertured film can be made to form a fluid pervious topsheet and/or the fluid impervious breathable backsheet.

U.S. Patent Application No. 2006/0087053 published Apr. 27, 2006 discloses a method for making apertures in a precursor web by moving the web material through a nip of the counter-rotating, intermeshing rollers, wherein a first roller comprises circumferentially-extending ridges and grooves, and a second roller comprises teeth being tapered from a base to a tip which are joined to the second roller at the base. The base of the tooth has a cross-sectional length dimension greater than a cross-sectional width dimension. Apertures are formed in the precursor web material as the teeth on one of the rollers intermesh with grooves on the other of the rollers. The process provides an efficient and cost effective means of forming apertures in a web; however, the size and shape of the apertures is limited by the shape and orientation of the teeth in the second roller as well as the orientation of the long chain molecules forming the film. For instance, extruded films have molecular orientations where a majority of the long chain molecules are oriented in the machine direction, which for an extruded film is the path that the film follows through the extrusion process. The cross sectional length of the teeth on the second roller of the counter rotating rollers is also aligned in the machine direction. As a result, when forming apertures in extruded films, the process tends to produce apertures resembling slits. Although slits may be acceptable for some applications, apertures resembling oval holes are typically preferred.

Accordingly, there is a need for a process for producing apertures in a film or film nonwoven laminate that can overcome the effect of film molecular orientation and produce apertures resembling oval holes rather than slits.

SUMMARY OF THE INVENTION

A method for making apertures in a web is disclosed where the apertures produced in the web more closely resemble an oval hole rather than a slit. The resulting web exhibits improved fluid acquisition capability, compression resistance and aesthetics.

DETAILED DESCRIPTION OF THE INVENTION

Figure 1:
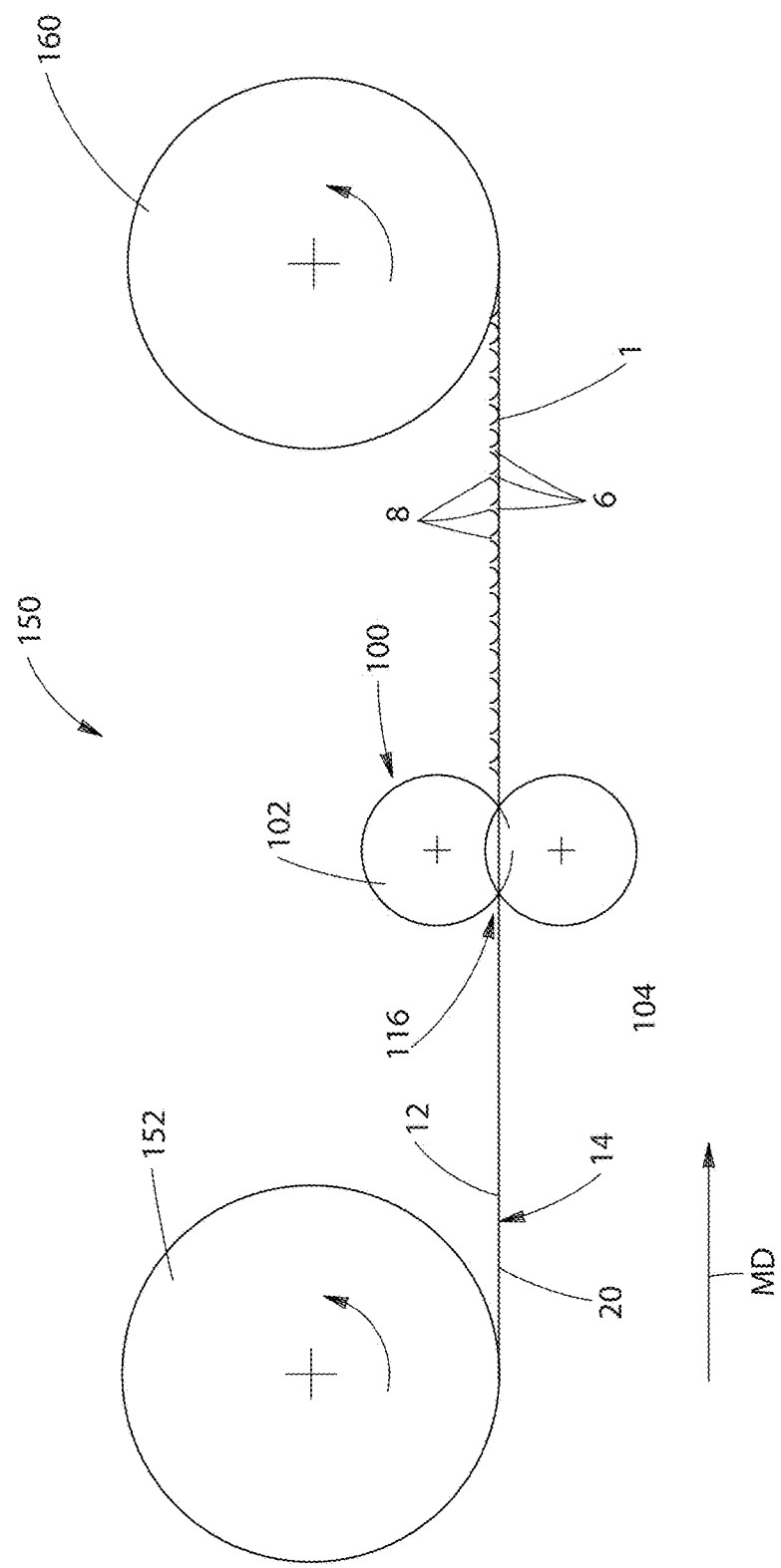
FIG. 1 is a schematic representation of a process of the present invention.

Definitions:

As used herein and in the claims, the term "comprising" is inclusive or open-ended and does not exclude additional unrecited elements, compositional components, or method steps.

"Machine direction" or "MD" is the direction parallel to the direction of travel of the web as it moves through the manufacturing process. Directions within ±45 degrees of the MD are considered to be machine directional.

The "cross machine direction" or "CD" is the direction substantially perpendicular to the MD and in the plane generally defined by the web. Directions within 45 degrees of the cross direction are considered to be cross directional.

As used herein the term "activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, a reduction in basis weight, and/or controlled fiber destruction in the intermediate web sections. For example, a common activation method is the process known in the art as ring rolling.

As used herein the term "activation member" means a device including teeth and grooves for performing activation.

As used herein the term "deformation zone" means an area where teeth and grooves of opposing activation members intermesh causing activation.

As used herein the term "path length" means the length of the deformation zone formed by intermeshing teeth and grooves of opposing activation members.

As used herein "depth of engagement" means the extent to which intermeshing teeth and grooves of opposing activation members extend into one another.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 6 gsm to 400 gsm, depending on the ultimate use of the web. For use as a hand towel, for example, both a first web and a second web can be a nonwoven web having a basis weight of between 18 gsm and 500 gsm.

The constituent fibers of a nonwoven web can be polymer fibers, and can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven web may also be a mixture of different fiber types, differing in such features as chemistry (e.g. PE and PP), components (mono- and bi-), denier (micro denier and >20 denier), shape (i.e. capillary and round) and the like. The constituent fibers can range from about 0.1 denier to about 100 denier.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multiconstituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and may be fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

As used herein, the term "molecular orientation" describes the degree to which the polymer chains or crystals lie along a particular direction.

As used herein the term "predominant molecular orientation" describes the degree to which a majority of the polymer chains lie along a particular direction.

As used herein the term "plastic deformation" is deformation that remains in a material after the load causing the deformation is removed. Plastic deformation is the permanent part of the deformation beyond an elastic limit of a material.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

The present invention will be described with respect to a method and apparatus used for making an apertured web. The apertured web can be an apertured film or an apertured laminate comprising a film and nonwoven. Apertures can include micro apertures and macro apertures, the former being substantially invisible to the unaided naked eye of an observer from approximately 1 meter away in ordinary indoor lighting and the latter being visible under such conditions. Micro apertures and/or other embossing or texturing can be formed prior to processing by the apparatus of the present invention. Apertured web can be used in disposable absorbent articles such as bandages, wraps, incontinence devices, diapers, sanitary napkins, pantiliners, tampons, and hemorrhoid treatment pads, as well as other consumer products such as floor cleaning sheets, body wipes, and laundry sheets. In addition, webs of the present invention can be utilized as perforated webs in automotive, agricultural, electrical, or industrial applications.

One apparatus of the present invention is shown schematically in FIG. 1. Precursor web 20 is moved in the machine direction (MD) to forming apparatus 150 where apertures 6 are formed producing apertured web 1. Precursor web 20 can be supplied from a supply roll 152 (or supply rolls, as needed for multiple web laminates) or any other supply means, such as festooned webs, as is known in the art. In one embodiment, precursor web 20 can be supplied directly from a web making apparatus, such as a polymer film extruder. Subsequent to formation, apertured web 1 can be taken up on a supply roll 160 for storage and further processing as a component in other products. Alternatively, apertured web 1 can be conveyed directly to further post processing, including a converting operation for incorporation into a finished product, such as a disposable absorbent product.

As shown in FIG. 1, apertured web 1 can be formed from a generally planar, two dimensional precursor web 20 having a first surface 12 and a second surface 14. Precursor web 20 can be a polymer film or a laminate of a polymer film and a nonwoven web. First surface 12 corresponds to a first side of precursor web 20, as well as a first side of apertured web 1. Second surface 14 corresponds to a second side of precursor web 20, as well as a second side of apertured web 1. In general, the term "side" is used herein in the common usage of the term to describe the two major surfaces of generally two-dimensional webs, such as films. Of course, in a composite or laminate structure, the first surface 12 of the apertured web 1 is the first side of one of the outermost layers or plies, and the second surface 14 is the second side of the other outermost layer or ply.

Precursor web 20 can be a polymeric film web. In one embodiment precursor web 20 can be a polymeric web suitable for use as a topsheet in a disposable absorbent product, as is known in the art. Polymeric film webs can be deformable. Deformable material as used herein describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials. The processes of the present invention are used to form materials comprising a polymeric film. Such materials include polymeric films alone or laminate comprising polymeric films and other materials such as nonwovens.

Deformable polymeric film webs utilized in the process of the present invention can have a transformation temperature range where changes in the solid state molecular structure of the material occur, such as a change in crystalline structure or a change from solid to molten state. As a consequence, above the transformation temperature range, certain physical properties of the material are substantially altered. For a thermoplastic semicrystalline film, the transformation temperature range may be the glass transition temperature range of the film, above which the polymer becomes rubbery and capable of elastic or plastic deformation without fracture or the melt temperature range of the film, above which the film is in a molten state and loses substantially all previous thermo-mechanical history.

Polymeric film webs can comprise thermoplastic polymers having characteristic rheological properties which depend on their composition and temperature. Below their glass transition temperature, such thermoplastic polymers can be quite hard and stiff and often brittle. Below this glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, the processes of the present invention can be utilized to form materials comprising thermoplastic polymer, especially thermoplastic film, which is within this viscoelastic temperature range.

Polymeric film webs can comprise a certain amount of ductility. Ductility, as used herein, is the amount of permanent, unrecoverable, plastic strain which occurs when a material is deformed, prior to failure (rupture, breakage, or separation) of the material. Ductility is dependent upon the rate of strain that is applied to the material. Materials formed in the process of the present invention can have a minimum ductility of at least about 10%, or at least about 50%, or at least about 100%, or at least about 200% or at least about 500%.

Polymeric film webs utilized in the present invention can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. Polymeric film webs can be single layered or multilayered flat films. As noted below, polymeric film webs can be textured, embossed, or otherwise altered from a strictly flat, planar configuration.

Physical properties of polymeric films, in particular the modulus, depend on polymer molecular orientation which is previously defined as the degree to which polymer chains lie along a particular direction. The molecular orientation of a film can be determined according to ASTM method D2732-03. The test method covers determination of the degree of unrestrained linear thermal shrinkage at given specimen temperature of plastic film and sheeting of 0.030 in (0.76 mm) thickness or less. Film specimens having a predominant molecular orientation will shrink primarily in the direction of the predominant molecular orientation and to a lesser extent in the direction perpendicular thereto.

A biaxially oriented polymeric film has a substantially random orientation with respect to the MD and the CD. By "substantially random molecular orientation" it is meant that due to conditions during film processing, there is not a significantly higher amount of long chain molecules oriented in the MD than in the CD. In other words the number of long chain molecules in the MD and the CD is about the same. As a result, films having a random molecular orientation can exhibit similar properties, such as modulus, in the MD and the CD. A blown film can be an example of a biaxially oriented polymeric film. In contrast, films having a predominant molecular orientation have a higher amount of long chain molecules oriented in a particular direction. For instance, extruded films can have a higher amount of long chain molecules oriented in the MD than in the CD. A cast film is an example of a film that has a predominant molecular orientation in the MD. The molecular orientation of a polymeric film can be modified by heating and/or plastically deforming the film. For instance, a film having a predominant molecular orientation in the MD can be strained and plastically deformed in the CD changing the orientation of the long chain polymers to a biaxial or CD oriented polymeric film.

Precursor web 20 can be a composite or a laminate of two or more precursor webs, and can comprise, for example, a combination of polymer films and nonwoven webs. Nonwoven webs or fabrics have been formed from many known processes, such as, for example, air laying processes, melt-blowing processes, spunbonding processes, hydroentangling processes, spunlacing processes, and bonded carded web processes. Also, multi-layer webs, such as spunbond-melt-blown-spunbond (SMS) webs and the like (e.g., SMMS, SSMS) made by multiple beam spunbond processes, can be utilized. It is not necessary that each component (i.e., the spunbond or meltblown components) be the same polymer. Therefore, in an SMS web, it is not necessary that the spunbond and the meltblown layers comprise the same polymer.

The constituent fibers of nonwoven webs can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from 0.1-500 microns in 1 micron increments.

Precursor web 20 can be preheated by means known in the art, such as by radiant heating, forced air heating, convection heating, or by heating over oil-heated rollers. Precursor web 20 can be pre-printed with indicia, designs, logos, or other visible or invisible print patterns. For example, designs and colors can be printed by means known in the art, such as by ink-jet printing, gravure printing, flexographic printing, or offset printing, to change the color of at least portions of precursor web 20. In addition to printing, precursor web 20 can be treated with coatings, such as with surfactants, lotions, adhesives, and the like. Treating precursor web 20 can be achieved by means known in the art such as by spraying, slot coating, extruding, or otherwise applying coatings to one or both surfaces.

Supply roll 152 rotates in the direction indicated by the arrow in FIG. 1 as precursor web 20 is moved in the machine direction by means known in the art, including over or around any of various idler rollers, tension-control rollers, and the like (all of which are not shown) to the nip 116 formed by a pair of counter-rotating, intermeshing rolls 102 and 104. The pair of intermeshing rolls 102 and 104 operate to form apertures in web 20 forming apertured web 1. Intermeshing rolls 102 and 104 are more clearly shown in FIG. 2.

Figure 2:
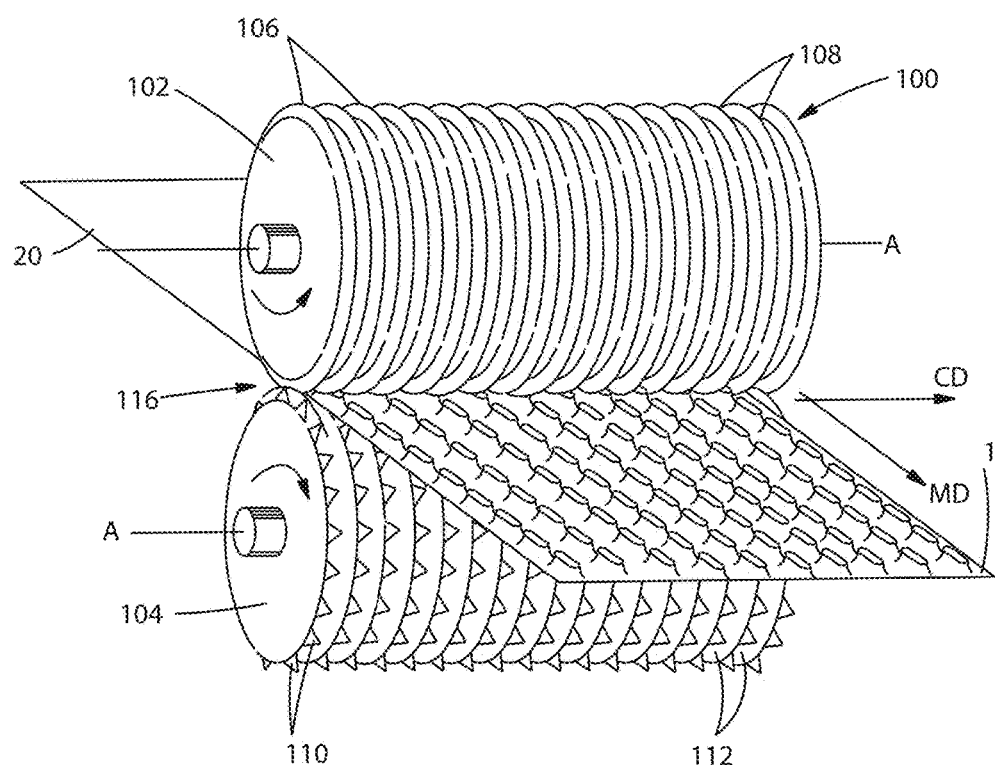
FIG. 2 is perspective representation of an apparatus of the present invention.
Figure 8:
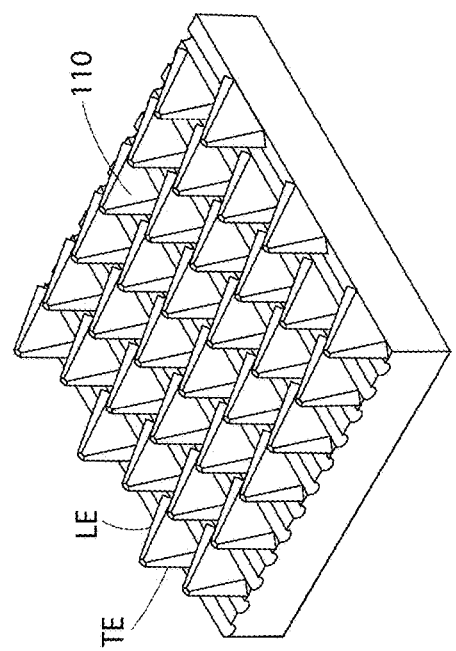
FIG. 8 is a perspective view of a portion of the apparatus shown in FIG. 2.

Referring to FIG. 2, there is shown in more detail the portion of forming apparatus 150 for making apertures in apertured web 1. This portion of apparatus 150 is shown as forming apparatus 100 in FIG. 2, and comprises a pair of steel intermeshing rolls 102 and 104, each rotating about an axis A, the axes A being parallel and in the same plane. Forming apparatus 100 can be designed such that precursor web 20 remains on roll 104 through a certain angle of rotation, as shown in detail below with respect to FIG. 8, but FIG. 2 shows in principle what happens as precursor web 20 goes straight through nip 116 on forming apparatus 100 and exits as apertured web 1. Therefore, while FIG. 2 shows apertured web 1 going straight into and coming straight out of nip 116, precursor web 20 or apertured web 1 can be partially wrapped on either of rolls 102 or 104 through a predetermined angle of rotation prior to (for precursor web 20) or after (for apertured web 1) nip 116. For example, after exiting nip 116, apertured web 1 can be directed to be wrapped on roll 104 through a predetermined angle of rotation such that the apertures remain resting over, and "fitted" onto, teeth 110 of roll 104, as shown in FIG. 8.

Rollers 102 and 104 can be made of steel or aluminum. In one embodiment, the rollers can be made of stainless steel. In general, rollers 102 and 104 can be made of corrosion resistant and wear resistant steel.

Roll 102 can comprise a plurality of ridges 106 and corresponding grooves 108 which can extend unbroken about the entire circumference of roll 102. In some embodiments, depending on what kind of pattern is desired in apertured web 1, roll 102 can comprise ridges 106 wherein portions have been removed, such as by etching, milling or other machining processes, such that some or all of ridges 106 are not circumferentially continuous, but have breaks or gaps. The breaks or gaps can be arranged to form a pattern, including simple geometric patterns such as circles or diamonds, but also including complex patterns such as logos and trademarks. In one embodiment, roll 102 can have teeth, similar to the teeth 110 on roll 104, described more fully below. In this manner, it is possible to have three dimensional apertures having portions extending outwardly on both sides of apertured web 1. In addition to apertures, various out-of-plane macro-areas of apertures of web 1 can be made, including macro-patterns of embossed texture depicting logos and/or designs. In an alternate embodiment, the outer surface of roll 102 can comprise a brush or elastic material such as rubber which allow teeth on mating roll 104 to penetrate at a nip formed between the two rolls.

Alternatively, roll 102 may be replaced with a brush conveyor as disclosed in U.S. Pat. No. 5,802,682 issued to Jourde, et al. Sep. 8, 1998. For this embodiment the brush conveyor may be arranged to interface with the teeth on mating roll 104 such that the teeth penetrate the brush at a nip formed between roll 104 and the brush conveyor.

Roll 104 is similar to roll 102, but rather than having ridges that can extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 7, discussed below. Both or either of rolls 102 and 104 can be heated by means known in the art such as by incorporating hot oil filled rollers or electrically-heated rollers. Alternatively, both or either of the rolls may be heated by surface convection or by surface radiation.

Teeth 110 can be joined to roller 104. By "joined" is meant that teeth can be attached to, such as by welding, compression fit, or otherwise joined. However, "joined" also includes integral attachment, as is the case for teeth machined by removing excess material from roller 104. The location at which teeth 110 are joined to roller 104 is the base. At any cross-sectional location parallel to the base each tooth can have a non-round cross-sectional area. In the circumferential direction a cross-sectional length of the cross-sectional area (corresponding to the tooth length, as discussed below), is at least two times a cross sectional width, measured perpendicular to the length dimension at the center of the cross-sectional area. In an alternate embodiment the teeth may comprise pins that are cylindrical, rectangular or other shapes depending on the corresponding aperture shape desired.

Figure 3:
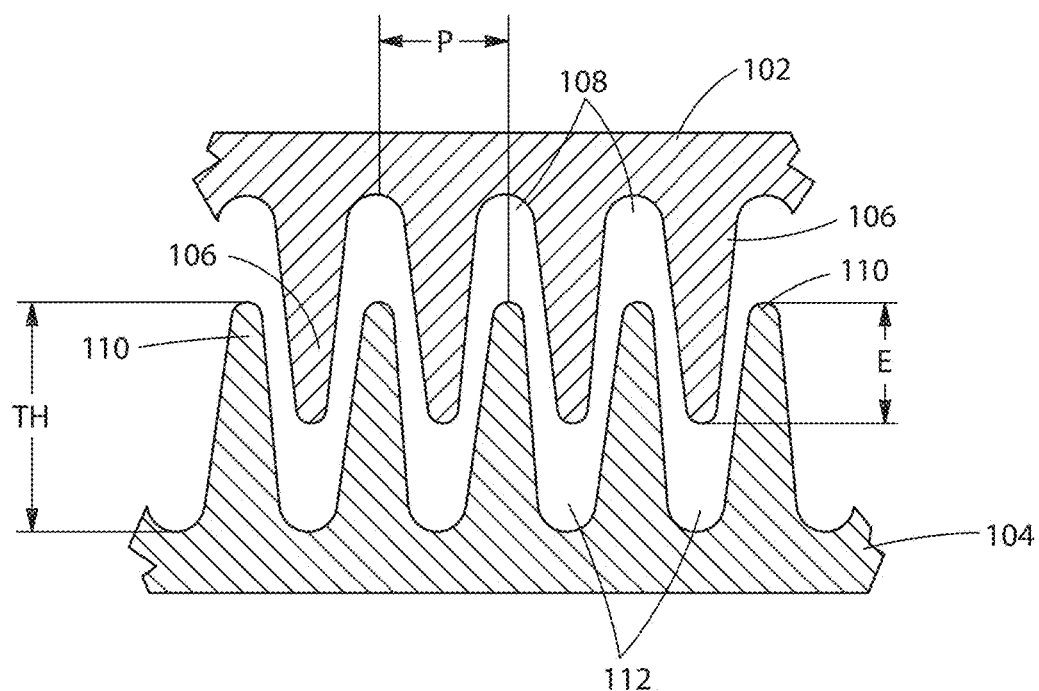
FIG. 3 is a cross-sectional representation of a portion of the apparatus shown in FIG. 2.

FIG. 3 shows in cross section a portion of the intermeshing rolls 102 and 104 including ridges 106 and representative teeth 110. As shown, teeth 110 have a tooth height TH (note that TH can also be applied to ridge 106 height; in a preferred embodiment tooth height and ridge height are equal), and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of precursor web 20 and the desired characteristics of apertured web 1 of the present invention. For example, in general, to obtain a higher density of volcano-shaped structures 8 or apertures 6 of web 1, the smaller the pitch should be, and the smaller the tooth cross sectional length TL and tooth spacing distance TD should be, as described below.

It is also contemplated that the size, shape, orientation and spacing of the teeth 110 can be varied about the circumference and width of roll 104 to provide for varied apertured web 1 properties and characteristics.

Additionally, substances such as lotions, ink, surfactants, and the like can be sprayed, coated, slot coated, extruded, or otherwise applied to apertured web 1 before or after entering nip 116. Any processes known in the art for such application of treatments can be utilized.

Figure 4:
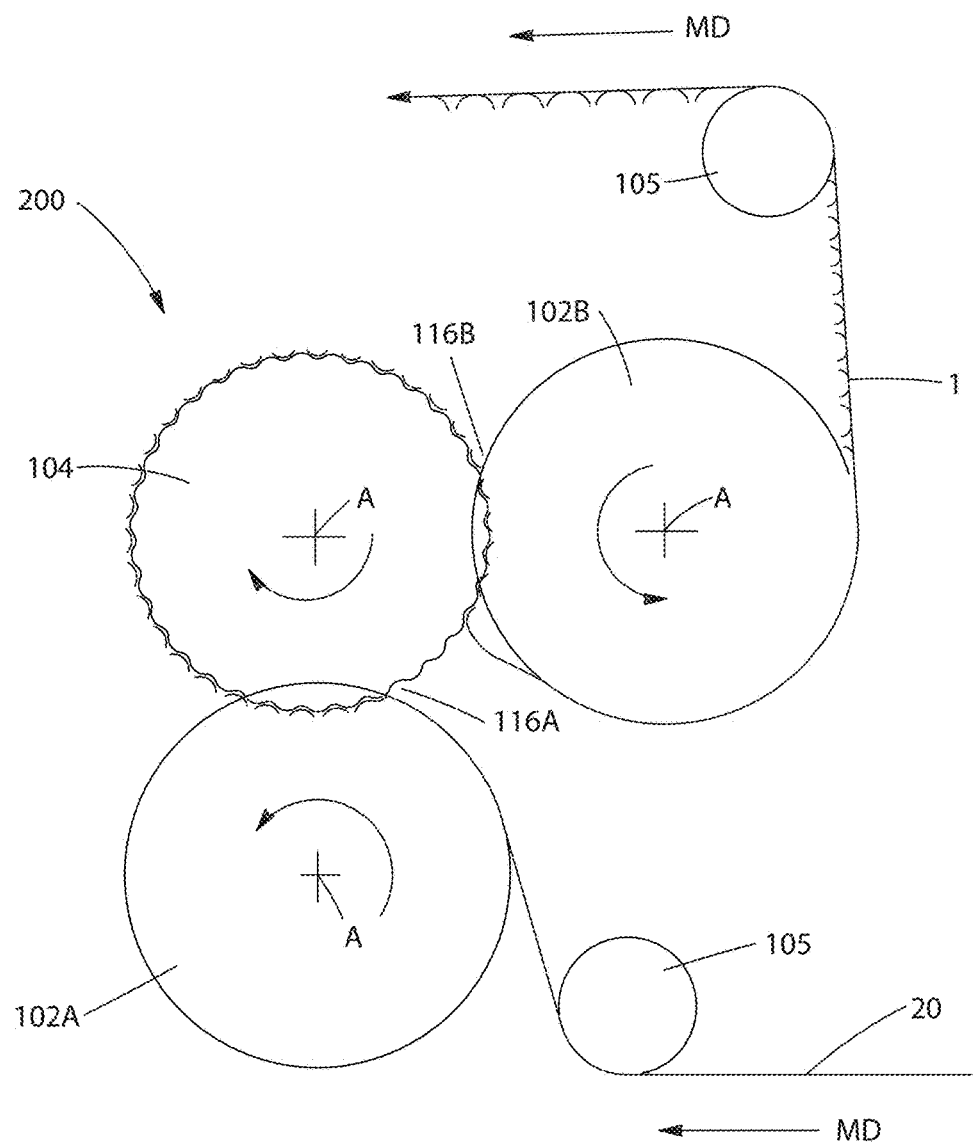
FIG. 4 is a schematic representation of another embodiment of a process and apparatus of the present invention.

In one embodiment, apertured web 1 can be formed by processing a precursor web 20 through an apparatus 200 as shown in FIG. 4. The multi-roller arrangement of apparatus 200 is designed to provide for a predetermined dwell time in which apertured web 1 remains in contact with toothed roller 104 through a predetermined angle of rotation. While the angle of rotation can be optimized depending upon the type of film, temperature of rollers, and the speed of web travel, in general the angle of wrap can be at least 10 degrees and as high as about 270 degrees or more, depending, at least in part, on the relative sizes of the mating rollers. As shown, precursor web 20 can be guided around various guide rollers and tensioning members (not shown) to guide roller 105 and onto roll 102A which can have ridges and grooves as described with respect to roller 102 of apparatus 150 in FIG. 1 above. Roller 102A can be heated to aid in forming volcano-shaped structures 8 and apertures 6. In one embodiment, roller 102 can be heated to about 200° F.

As shown in FIG. 4, precursor web 20 enters nip 116A formed by the inter-engagement of meshing rollers 104 and 102A. Roller 104 of apparatus 200 can be a toothed roller as described above with respect to apparatus 150 in FIG. 1. As precursor web 20 passes through nip 116A, teeth 110 on roller 104 press into and/or through and can pierce precursor web 20 to form volcano-shaped structures 8 and apertures 6. Apertured web 1 then continues in stationary contact with rotating roller 104 until reaching nip 116B formed by the inter-engagement of roller 104 with roller 102B. Roller 102B can have ridges and grooves as described with respect to roller 102 of apparatus 150 in FIG. 1 above.

As apertured web 1 exits nip 116B it is directed off of roller 104, onto roller 102B and over various guide rollers 105 as necessary before being wound for further processing, shipping, or placement for incorporation in a manufactured product. In one embodiment, apertured web 1 is directed into a manufacturing process for sanitary napkins, wherein apertured web 1 is fed into the process as a topsheet and joined to other components such as a backsheet web, cut to finished shape, packaged, and shipped to retail outlets. In another embodiment, the web is directed into a manufacturing process for a diaper product, wherein apertured web 1 is fed into the process as a backsheet and joined to other components such as a topsheet.

If apertured web 1 tends to stick to teeth 110 upon being pulled off of roller 104, various processing aids can be added as necessary. For example, non-stick treatments, such as silicone or fluorocarbon treatments can be added. Various lubricants, surfactants or other processing aids can be added to the precursor web 20 or to the roller 104. Other methods of aiding the removal of the web from the roller include air knives or brushing. In one embodiment, roller 104 can have an internal chamber and means to provide positive air pressure at the point of web removal onto roller 102B. In general, control of the transition from roller 104 to roller 102B is affected by web speed, relative roller speeds (i.e., tangential speed of roller 104 and roller 102B), web tension, and relative coefficients of friction. Each of these parameters can be varied as known by those skilled in the art to ensure the desired transfer of apertured web 1 onto roller 102B.

The benefit of having an apparatus like that shown in FIG. 4 is that apertured web 1 experiences an extended amount of time in contact with and "nested" on teeth 110 of roller 104. In this manner, volcano-shaped structures 8 and apertures 6 have additional time to set and a higher likelihood of retaining a three-dimensional configuration once removed from roller 104. Without being bound by theory, it is believed that by adjusting the circumference of roller 104, the temperature of rollers 102A, 104, and/or 102B, as well as the coefficient of friction of rollers, this longer dwell time can be used to increase the line speed at which apertured web 1 can be processed to make permanent three-dimensional volcano-shaped structures 8. The temperature of rollers 102A, 104, and/or 102B may all be at the same temperature or alternatively at different temperatures. For example, rollers 102A and 104 may be heated while roller 102B is at room temperature or below. In addition, the speeds of the various rollers may be maintained at the same speed, or alternately a speed differential between the rollers may be established.

If any of the rollers of the apparatus 150 or 200, as described above are to be heated, care must be taken to account for thermal expansion. In one embodiment, the dimensions of ridges, grooves, and/or teeth are machined to account for thermal expansion, such that the dimensions shown in FIG. 3 and dimensions described herein are dimensions at operating temperature.

Figure 5:
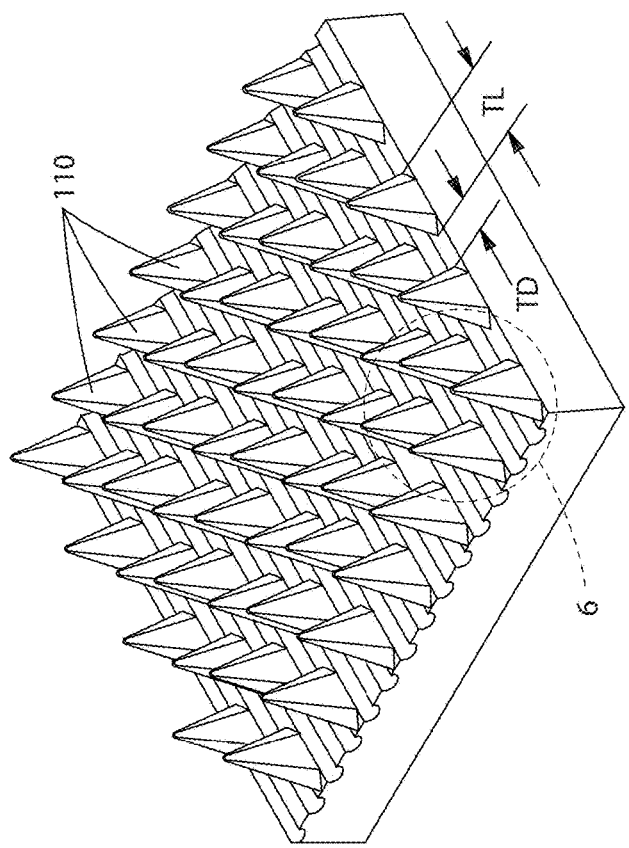
FIG. 5 is a perspective view of a portion of the apparatus shown in FIG. 2 or FIG. 8.
Figure 6:
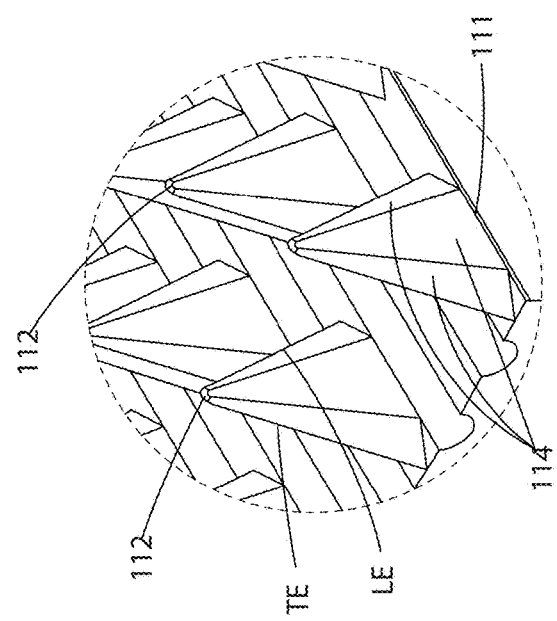
FIG. 6 is a magnified perspective view of a portion of the apparatus shown in FIG. 9.

FIG. 5 shows a portion of one embodiment of a roller 104 having a plurality of teeth 110 useful for making an apertured web 1. An enlarged view of the teeth 110 shown in FIG. 5 is shown in FIG. 6. As shown in FIG. 6, each tooth 110 has a base 111, a tooth tip 112, a leading edge LE and a trailing edge TE. The tooth tip 112 can be generally pointed, blunt pointed, or otherwise shaped so as to stretch and/or puncture the precursor web 20. Teeth 110 can have generally flattened blade-like shape. That is, as opposed to round, pin-like shapes that are generally round in cross section, teeth 110 can be elongated in one dimension, having generally non-round, elongated cross-sectional configurations. For example, at their base 111, the cross section of teeth 110 can have a tooth length TL and a tooth width TW exhibiting a tooth aspect ratio AR of TL/TW of at least 2, or at least about 3, or at least about 5, or at least about 7, or at least about 10 or greater. In one embodiment, the aspect ratio AR of cross-sectional dimensions remains substantially constant with tooth height.

In one embodiment of roller 104, teeth 110 can have a uniform cross sectional length dimension TL of about 1.25 mm measured generally from the leading edge LE to the trailing edge TE at the base 111 of the tooth 110, and a tooth cross sectional width TW of about 0.3 mm measured generally perpendicularly to the circumferential length dimension at the base. Teeth can be uniformly spaced from one another circumferentially by a distance TD of about 1.5 mm. For making a soft, fibrous three-dimensional apertured web 1 from a precursor web 20 having a basis weight in the range of from about 5 gsm to about 200 gsm, teeth 110 of roll 104 can have a length TL ranging from about 0.5 mm to about 3 mm, a tooth width TW of from about 0.3 mm to about 1 mm, and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH).

Of course, depth of engagement E, pitch P, tooth height TH, spacing TD and tooth cross sectional length TL can each be varied independently of each other to achieve a desired size, spacing, and area density of apertures 6 (number of aperture 6 per unit area of apertured web 1). For example, to make apertured films and nonwovens suitable for use in sanitary napkins and other absorbent articles, tooth cross sectional length TL at the base can range between about 2.032 mm to about 3.81 mm; tooth width TW can range from about 0.508 mm to about 1.27 mm; tooth spacing TD can range from about 1.0 mm to about 1.94 mm; pitch P can range from about 1.106 mm to about 2.54 mm; and tooth height TH can be from about 2.032 mm to about 6.858 mm Depth of engagement E can be from about 0.5 mm to about 5 mm. The radius of curvature R of the tooth tip 112 can be from 0.001 mm to about 0.009 mm Without being bound by theory, it is believed that tooth length TL at the base can range between about 0.254 mm to about 12.7 mm; tooth width TW can range from about 0.254 mm to about 5.08 mm; tooth spacing TD can range from about 0.0 mm to about 25.4 mm (or more); pitch P can range from about 1.106 mm to about 7.62 mm; tooth height TH can range from 0.254 mm to about 18 mm; and depth of engagement E can range from 0.254 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments).

Without wishing to be bound by theory, and consistent with currently-pending tool designs, it is believed that other dimensions are possible for use in the method and apparatus of the present invention. For example, tooth length TL at the base can range can be from about 0.254 mm to about 12.7 mm, and can include 4.42 mm, 4.572 mm and about 5.56 mm; tooth width TW can range from about 0.254 mm to about 5.08 mm, and can include 1.78 mm; tooth spacing TD can range from about 0.0 mm to about 25.4 mm, and can include 2.032 mm; pitch P can range from about 1.106 mm to about 7.62 mm; tooth height TH can range from 0.254 mm to about 18 mm, and can include 5.08 mm; and depth of engagement E can range from 0.254 mm to about 6.35 mm Radius of curvature can range from about 0.00 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments).

Figure 10:
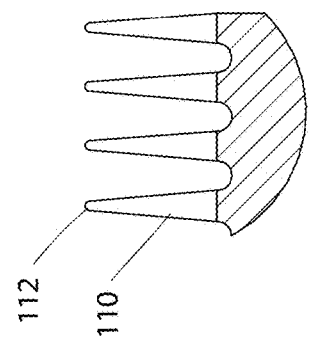
FIG. 10 is a plan view of a portion of the apparatus shown in FIG. 12.

In one embodiment, to make the volcano-shaped structures 8 and/or apertures 6 of apertured web 1, the LE and TE should taper to a point in a generally pyramidal or frustro-conical shape which can be described as being shaped like a shark's tooth. As shown in FIG. 10, the generally pointed pyramidal shark tooth shape can have six sides 114, each side being generally triangular in shape. The vertex of two sides makes up the leading edge LE and the vertex of two sides makes up the trailing edge TE of tooth 110. The vertices of the leading or trailing edge can be relatively sharp, or can be machined to have a rounded radius of curvature. The radius of curvature of the tooth tip can be 0.005 inches.

Figure 7:
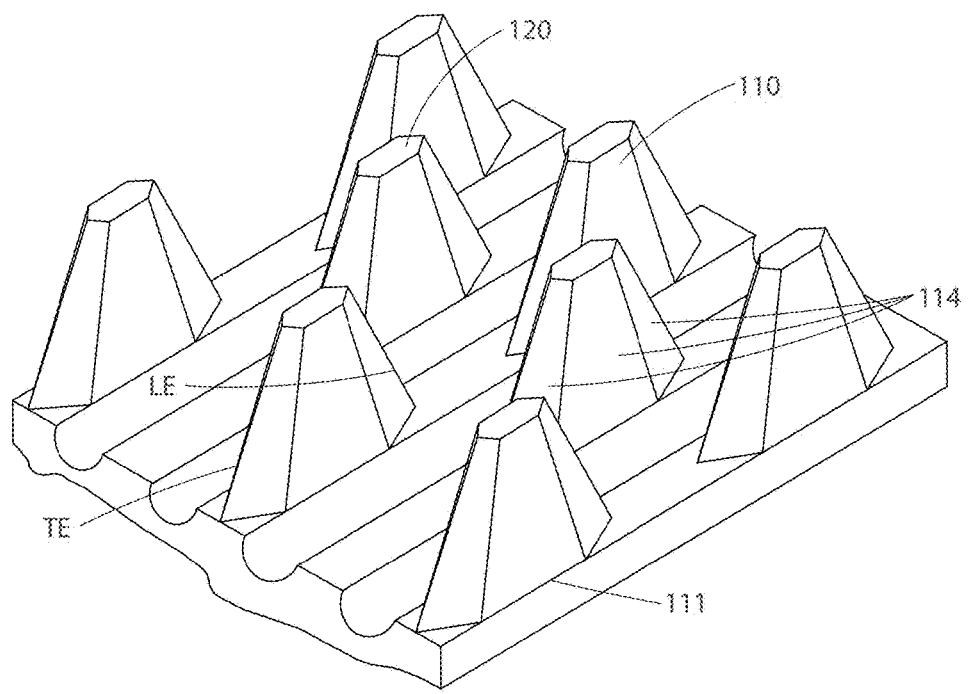
FIG. 7 is a perspective view of an alternative configuration for teeth on the apparatus shown in FIG. 2.

Other tooth shapes can be utilized to make apertures. As shown in FIG. 7, for example, the generally pyramidal shapes shown in FIG. 5 can be truncated so as to remove the pointedness of tips 112. Truncation can be made at a predetermined distance from base 111 such that a generally flattened region 120 is produced at the distal end of tooth 110. Generally flattened region 120 can have an area shape corresponding to the cross-sectional shape of tooth 110. Thus, generally flattened region 120 can also be elongated, that is, having a length dimension greater than a width dimension and an aspect ratio AR corresponding to the aspect ratio of tooth 110. In one embodiment, flattened region 120 can transition to sides 114 at generally sharp vertices, or the transition can be at a radius of curvature, providing for a smooth, rounded, flattened tooth tip.

In another embodiment, as shown in FIG. 8, teeth 110 can have at least one edge that extends generally perpendicularly with respect to the surface of roller 104. As shown in the partial perspective view of roller 104 in FIG. 8, for example, teeth resembling shark fins can have a leading edge LE that angles toward tip tooth 112, and a trailing edge TL that extends generally perpendicular from base 111 toward tip tooth 112. In another embodiment, the tooth 110 can have the same shape, but the leading and trailing edges reversed such that the generally perpendicular edge is the leading edge.

Figure 9:
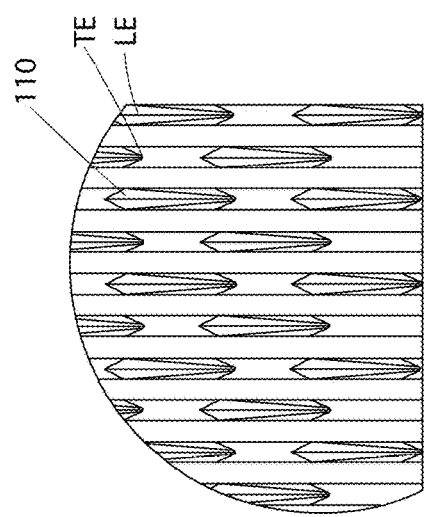
FIG. 9 is a top view of the portion of the apparatus shown in FIG. 12.

FIG. 9 is a top view of the portion of roller 104 shown in FIG. 8. Various dimensions are shown in the illustrated embodiment, including the angles produced by the sides 114 making up the leading and trailing edges. Likewise, FIG. 10 is a detail of the teeth shown in FIG. 8 showing representative dimensions. In general, while the dimensions shown are those currently believed to be beneficial for making three-dimensional formed films useful as topsheets on disposable absorbent articles, all dimensions can be varied as necessary depending on the desired aperture density, spacing, size, and the web type of precursor web 20.

Without being bound by theory, it is believed that having relatively sharp tips on teeth 110 permits the teeth 110 to punch through precursor web 20 "cleanly", that is, locally and distinctly, so that the resulting apertured web 1 can be described as being predominantly "apertured" rather than predominantly "embossed". In one embodiment, puncture of precursor web 20 is clean with little deformation of web 20, such that the resulting web is a substantially two-dimensional perforated web.

Apertured Film

Figure 11:
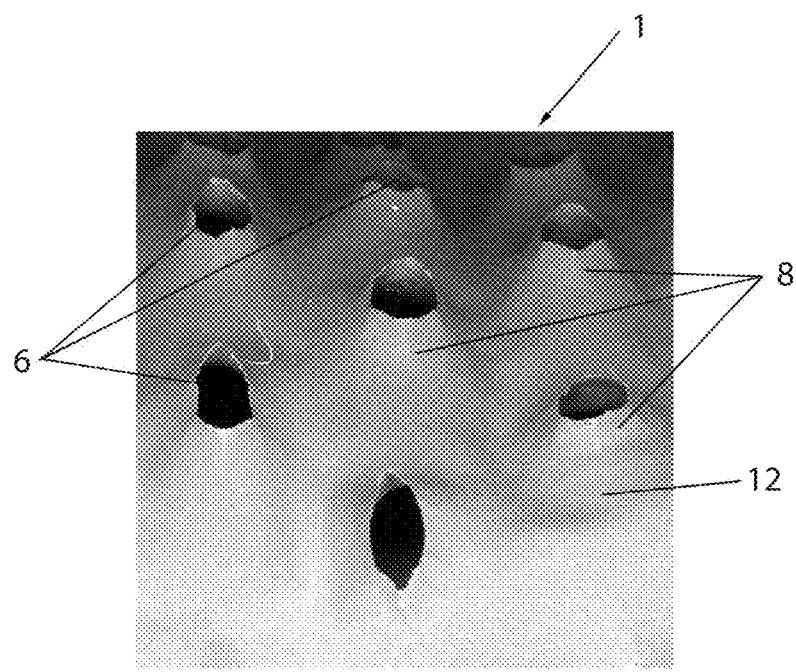
FIG. 11 is a photograph of a highly magnified portion of an apertured web made by the process of the present invention.

Two representative three-dimensional apertured formed film webs 1 are shown in the photomicrographs of FIGS. 11-14. FIG. 11 shows a portion of a three-dimensional, apertured web 1 made from a generally planar polyethylene film precursor web 20 having a basis weight of approximately 25 grams per square meter. Apertures 6 shown in FIG. 11 were formed by the action of teeth 110 on a heated roll 104 having stretched and pushed through precursor web 20 to permanently deform precursor web 20 to form a plurality of discrete, spaced apart volcano-like structures 8 extending outwardly from first side 12. Webs as shown in FIGS. 12-15 can be made by processing through the nip 116 of rolls 102 and 104 heated to about 200° F. In general, line speed and sufficient heating of apparatus 100 depends on the size of teeth 110, the angle of wrap on either roll, and/or the type and basis weight of the precursor web 20, all of which can be varied as necessary by means well known in the art.

Figure 12:
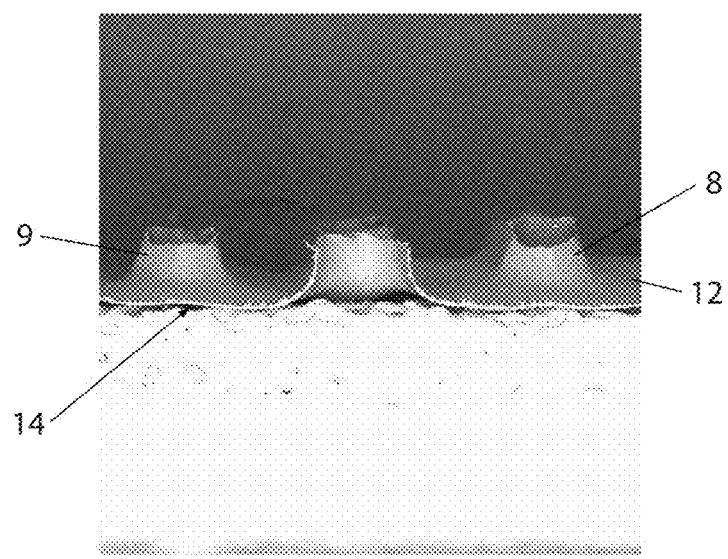
FIG. 12 is a cross-sectional view of the apertured web of FIG. 12.

As shown in the cross section of FIG. 12, apertures 6 place the first side 12 and the second side 14 of apertured web 1 in fluid communication through the volcano-like structures 8. Volcano-like structures 8 comprise a continuous side wall 9 of deformed film having a significant orientation in the Z-direction which can be relatively rigid to resist Z-direction compression in use. The undeformed portions of apertured web 1 of FIGS. 12 and 13 can be fluid impervious.

The number of apertures 6 per unit area of apertured web 1, i.e., the area density of apertures 6, can be varied from 1 aperture 6 per square centimeter to as high as 60 apertures 6 per square centimeter. There can be at least 10, or at least 20 apertures 6 per square centimeter, depending on the end use. In general, the area density need not be uniform across the entire area of apertured web 1, but apertures 6 can be only in certain regions of apertured web 1, such as in regions having predetermined shapes, such as lines, stripes, bands, circles, and the like. In one embodiment, where apertured web 1 is used as a topsheet for a sanitary napkin, for example, apertures 6 can be only in the region corresponding to the central part of the pad where fluid entry occurs.

As can be understood with respect to forming apparatus 100, therefore, apertures 6 of apertured web 1 are made by mechanically deforming precursor web 20 that can be described as generally planar and two dimensional. By "planar" and "two dimensional" is meant simply that the web is flat relative to apertured web 1 that has distinct, out-of-plane, Z-direction three-dimensionality imparted due to the formation of volcano-shaped structures 8. "Planar" and "two-dimensional" are not meant to imply any particular flatness, smoothness or dimensionality. As such, a soft, fibrous non-woven web can be planar in its as-made condition. As precursor web 20 goes through the nip 116 the teeth 110 of roll 104 enter grooves 108 of roll 102 and simultaneously urge material out of the plane of precursor web 20 to form permanent volcano-like structures 8 and apertures 6. In effect, teeth 110 "push" or "punch" through precursor web 20. As the tip of teeth 110 push through precursor web 20 the web material is urged by the teeth 110 out of the plane of precursor web 20 and is stretched and/or plastically deformed in the Z-direction, resulting in formation of permanent volcano-like structures 8 and apertures 6. The amount of ductility and other material properties of the precursor web, such as the glass transition temperature and crystallinity determine how much relatively permanent three-dimensional deformation the apertured web 1 retains.

Figure 13:
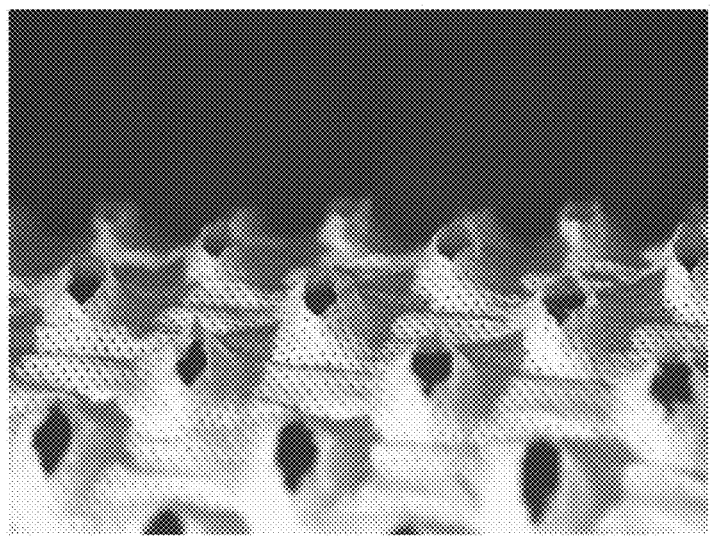
FIG. 13 is a photograph of a highly magnified portion of an apertured web made by the process of the present invention.
Figure 14:
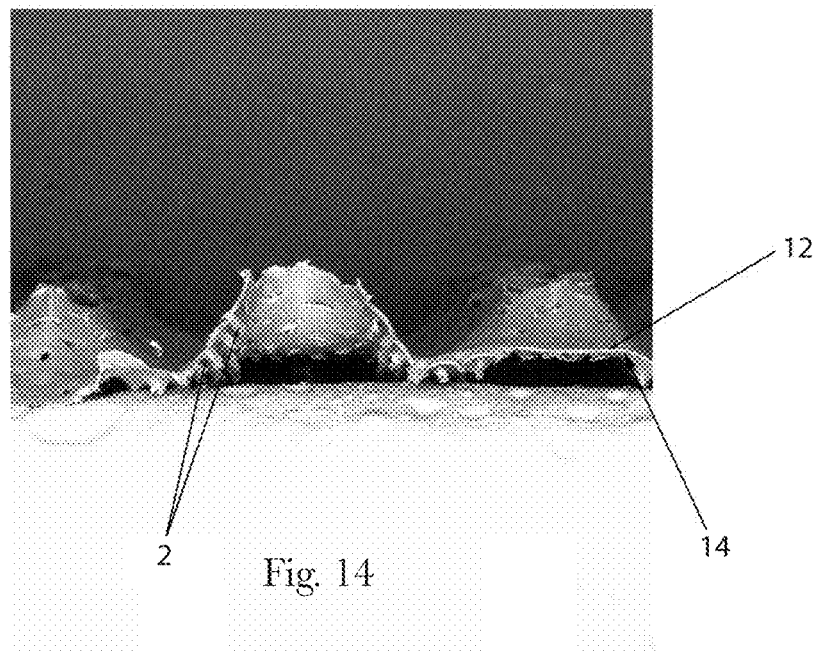
FIG. 14 is a cross-sectional view of the apertured web of FIG. 14.

FIGS. 13 and 14 show another embodiment of a three-dimensional apertured web 1 in which the precursor web 20 was not a flat film but rather was a film that was pre-textured with microscopic aberrations 2. Aberrations 2 can be bumps, embossments, holes, or the like. In the embodiment shown, aberrations 2 are also volcano-shaped micro-apertures, formed by a hydroforming process. A suitable hydroforming process is the first phase of the multiphase hydroforming process disclosed in U.S. Pat. No. 4,609,518, issued to Curro et al. on Sep. 2, 1986. The hydroforming screen utilized for the webs shown in FIGS. 14 and 15 was a "100 mesh" screen and the film was obtained from Tredegar Film Products, Terre Haute, Ind. Apertures 6 were formed by teeth 110 of roll 104 in apparatus 100.

As shown in the cross section of FIG. 14, in one embodiment apertures 6 formed by the teeth 110 of roll 104 extend in a direction away from first side 12 while the aberrations 2 such as the micro apertures formed by hydroforming extend away from second side 14. Aberrations 2 can also be non-apertured protrusions, fibrils, or embossments to provide texture that provides for a tactile impression of softness. Softness is beneficial when webs 1 are used as topsheets in disposable absorbent articles, and the method disclosed herein for forming volcano-shaped structures 8 and apertures 6 is effective in preserving the micro texture aberrations 2, particularly when the volcano-shaped structures 8 and apertures 6 are made on the disposable absorbent article production line. In this manner, a soft, compliant topsheet for a disposable absorbent article can be achieved when the apertured web 1 is used with the second side 14 having aberrations 2 as the body-facing surface of the article.

The apertures 6 of the film embodiments shown in FIGS. 11-14 were made on an apparatus like that shown in FIG. 2, where the apparatus 100 is arranged to have one patterned roll, e.g., roll 104, and one non-patterned grooved roll 102. However, in certain embodiments it may be preferable to form nip 116 by use of two patterned rolls having either the same or differing patterns, in the same or different corresponding regions of the respective rolls. Such an apparatus can produce webs with apertures 6 protruding from both sides of the apertured web 1, as well as macro-texture, e.g., aberrations, micro-apertures, or micro-patterns, embossed into the apertured web 1. Likewise, it may be desirable to have multiple apparatuses 100 such that apertured web 1 is re-processed to have additional structures 8 and/or apertures 6. For example, a higher area density of volcano-shaped structures 8 on apertured web 1 can be achieved by processing precursor web 20 through two or more apparatuses 100.

It is also contemplated that the size, shape, orientation and spacing of the teeth 110 can be varied about the circumference and width of roll 104 to provide for varied apertured web 1 properties and characteristics. The number, spacing, and size of apertures 6 can be varied by changing the shape, number, spacing, and size of teeth 110 and making corresponding dimensional changes as necessary to roll 104 and/or roll 102. This variation, together with the variation possible in precursor webs 20 and the variation in processing, such as line speeds, roll temperature, and other post processing variations, permits many varied apertured webs 1 to be made for many purposes.

While the size of apertures produced according to the process described herein is related to the corresponding size and shape of the teeth 110 as well as other aforementioned process parameters, it has been found that the actual shape of the apertures is related to the orientation of the teeth 110 on roll 104 relative to the molecular orientation of the long chain molecules forming precursor web 20. In other words, teeth disposed at an angle relative to the molecular orientation of the film have been found to form oval shaped apertures with aspect ratios (L/W) that are comparably less than the aspect ratios of elongate shaped apertures formed by teeth aligned parallel to the molecular orientation of the film. In fact teeth aligned perpendicular to the molecular orientation of the film have been found to form oval shaped apertures with aspect ratios (L/W) approaching 1.0 where as teeth aligned parallel to the molecular orientation of the film can form apertures with aspect ratios exceeding 5.0.

Not to be bound by theory, when a tooth punctures a film web, it cuts or breaks long chain molecules causing the molecules to pull apart. If the teeth are heated, stress relaxation or melting may occur, causing the long chain molecules to shrink while returning to a point of equilibrium. As a result, it is believed that MD oriented teeth effect fewer long chain molecules when puncturing the MD oriented film resulting in slits where as the CD oriented teeth effect more long chain molecules in the MD oriented film resulting in larger and more rounded apertures. Thus, it has been found that the formation of oval shaped apertures with minimal aspect ratios can be achieved by modifying the orientation of the teeth and/or the molecular orientation of the film so that the relative angle between the orientation of the teeth and molecular orientation of the film is greater than 0°, preferably the relative angle between the orientation of the teeth and molecular orientation of the film ranges from about 30° to about 90°. More preferably, the relative angle is about 90°.

For instance, the teeth 110 on roll 104 of forming apparatus 100 shown in FIG. 2 are oriented such that the teeth cross sectional length TL is aligned in the MD. Such MD aligned teeth can produce slitted or elongate shaped apertures in a film having a predominant molecular orientation in the MD. By comparison, if the teeth 110 were oriented such that the cross sectional length TL of the teeth were aligned in the CD, then the teeth would produce oval shaped apertures in a film having a predominant molecular orientation in the MD. Therefore, the orientation of the teeth on the roll can be arranged to produce apertures in an MD oriented film having minimal aspect ratio and preferably aspect ratios that are less than about 4.0.

EXAMPLE 1

Figure 15A:
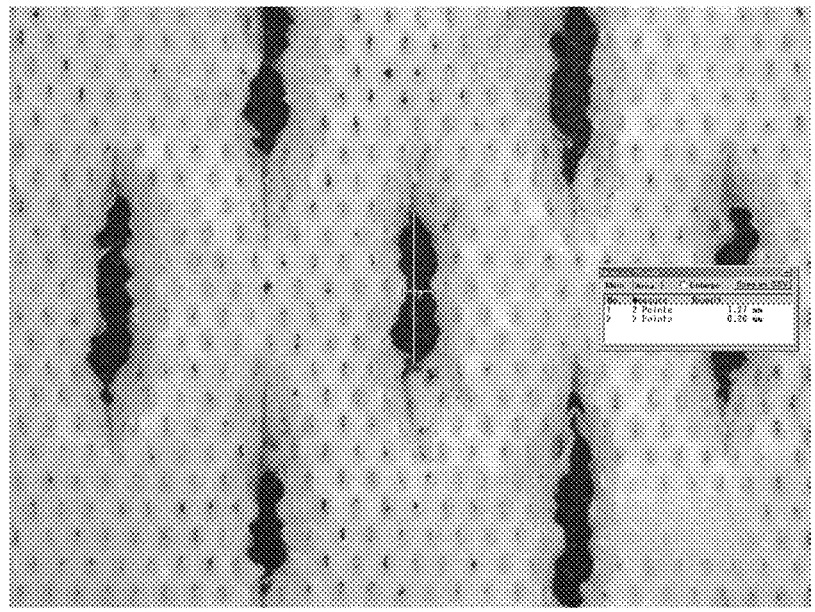
FIGS. 15a and 15b are photomicrographs of the apertures formed in samples 1 and 2, respectively, in Example 1.
Figure 15B:
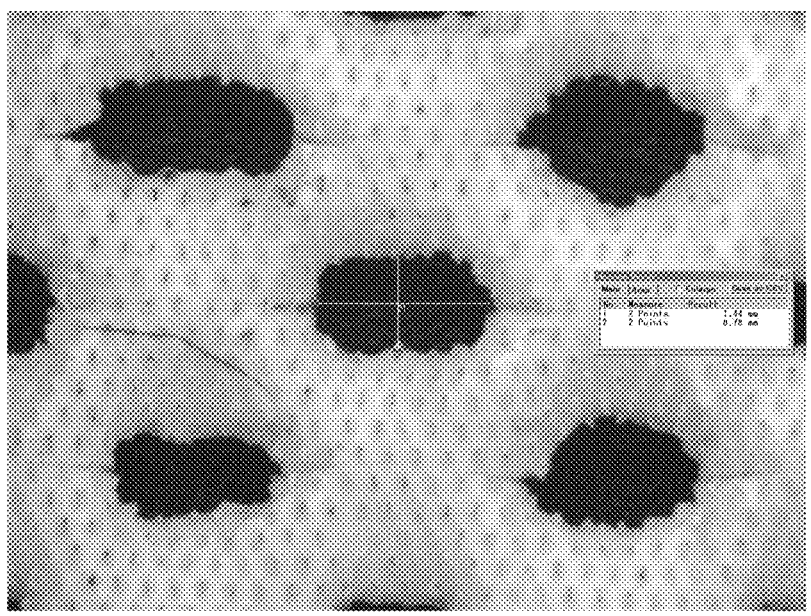
Figure 16A:
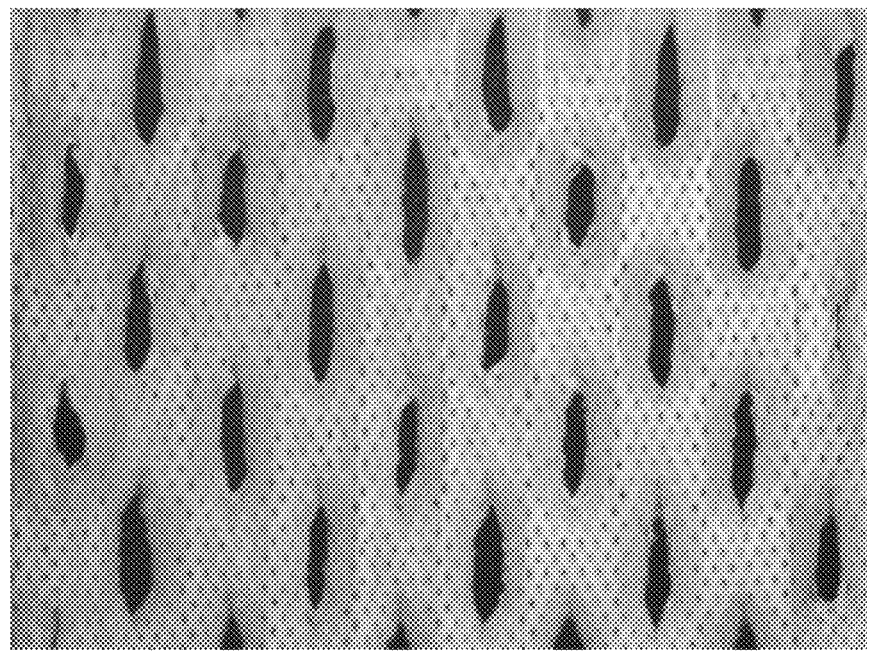
FIG. 16a through 16e are photomicrographs of the apertures formed in samples 3 through 7, respectively, in Example 2.
Figure 16B:
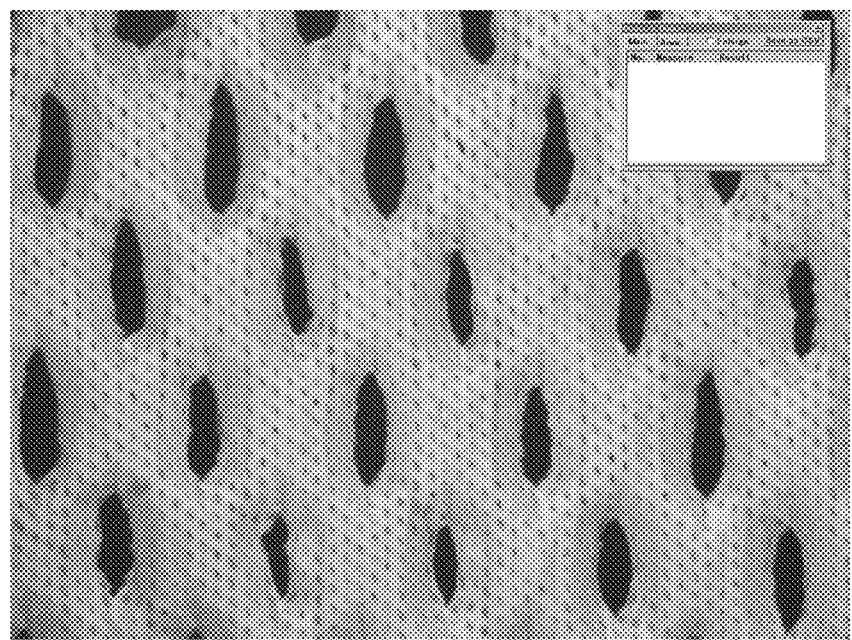
Figure 16C:
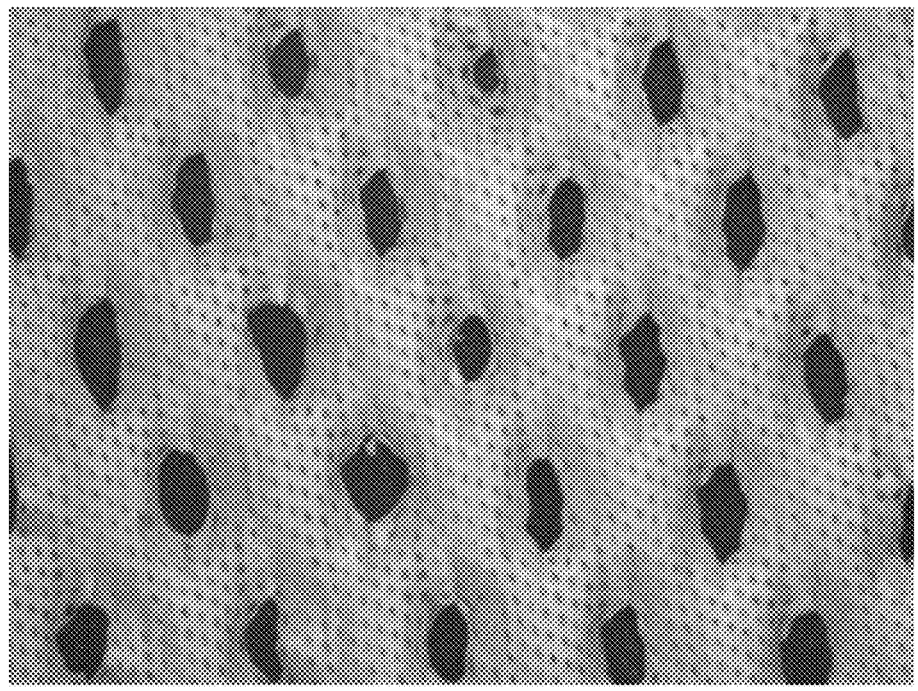
Figure 16D:
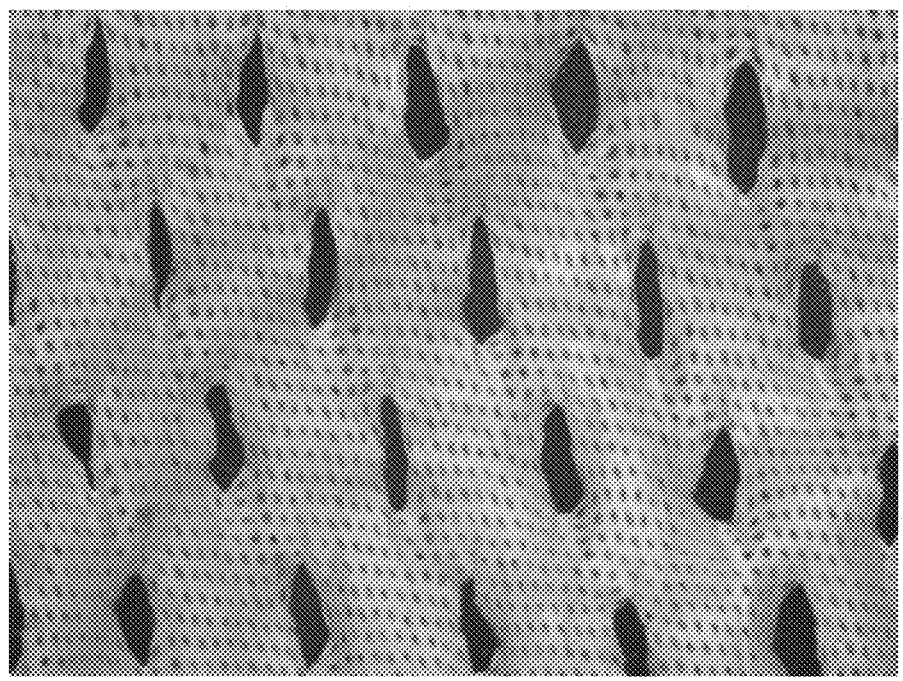
Figure 16E:
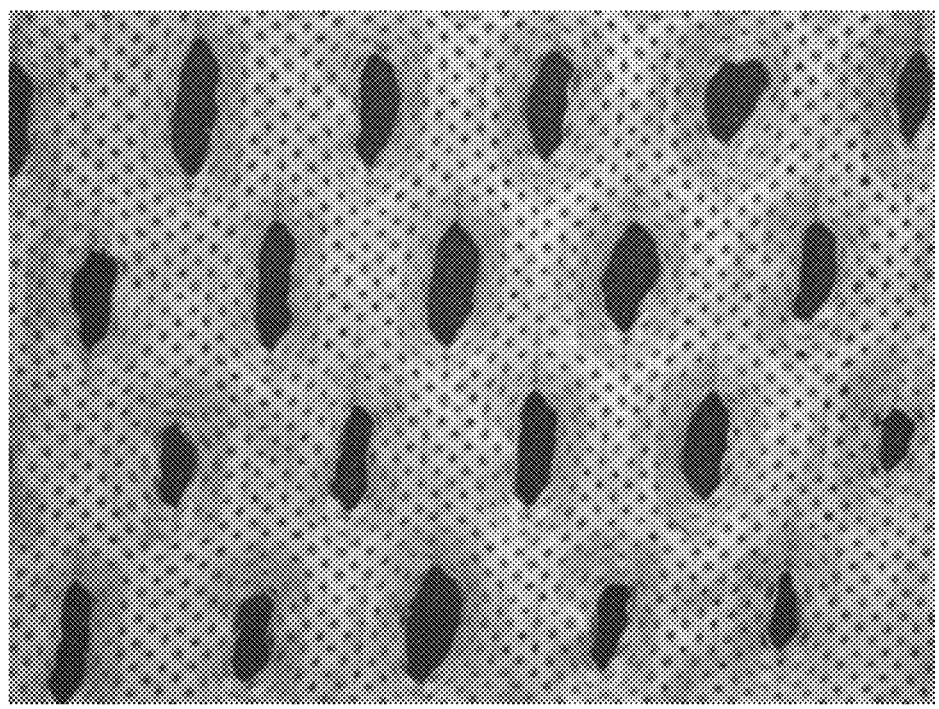

Samples were made by running micro apertured, 100 mesh films against 0.050 inch pitch forming apparatus. For sample 1, the teeth were oriented in the MD. For sample 2, the teeth were oriented in the CD. Both films were activated at a temperature of 75° C. and at a line speed of 50 feet/min. FIG. 15*a* of Sample 1 shows the resultant apertures produced by the MD oriented teeth and FIG. 15*b* of sample 2 is a result of orienting the teeth in the CD. As shown, the aperture length remains the same while the width is increased thereby decreasing the aspect ratio.

TABLE 1

| Sample | Average Aperture Length (mm) | Average Aperture Width (mm) | Average Aperture Aspect Ratio | FIG. |
|---|---|---|---|---|
| 1 | 1.43 | 0.28 | 5.1 | 15a |
| 2 | 1.44 | 0.81 | 1.8 | 15b |

EXAMPLE 2

Samples were apertured a by orienting the film samples relative to the teeth so that the effects of the orientation of the teeth relative to the molecular orientation of the film could be assessed. 100 mesh film samples were apertured using 0.050 inch pitch intermeshing plates on the high speed research press described in U.S. Pat. No. 7,024,939 and U.S. Pat. No. 7,062,983. Samples were cut into rectangular pieces (50 mm×200 mm) for testing. Five different samples were prepared, each cut at a different angle relative to the machine direction of the film. For sample 3, the sample was cut in alignment with the machine direction of the film, and so is designated to have an orientation angle of 0°. Sample 7 was cut with the long dimension of the sample aligned to the cross direction of the film and so is designated to have an orientation angle of 90°. Other samples were cut at 30, 45 and 60° relative to the machine direction of the film. For testing, the long dimension of the samples was aligned with the cross-sectional length dimension of the teeth on the intermeshing plates. In this way, the angle between the cross-sectional length dimension of the teeth, and the predominant molecular orientation (MD) of the film was varied to determine the impact on aperture quality. The temperature of both tooling plates was set at 100° C., and conditions were set up to mimic a 205.84 mm roll diameter, a web speed of 7.0 meters per second with 69 millisecond dwell time, and a depth of engagement of 2.39 mm Length and width of 10 apertures were measured and averaged and the aspect ratio calculated. Results are shown in the table below and demonstrate that the aspect ratio of samples apertured with teeth oriented at an angle relative to the machine direction of the film have a lower aspect ratio than those where the teeth and the machine direction of the film were aligned in the same direction. Photomicrographs of the apertures formed in samples 3 through 7 are shown in FIG. 16*a* through 16*e*, respectively.

TABLE 2

| Sample | Tooth Orientation Angle ° | Average Aperture Length (mm) | Average Aperture Width (mm) | Average Aperture Aspect Ratio | FIG. |
|---|---|---|---|---|---|
| 3 | 0 | 1.63 | 0.36 | 4.51 | 16a |
| 4 | 30 | 1.68 | 0.47 | 3.67 | 16b |
| 5 | 45 | 1.24 | 0.63 | 2.04 | 16c |
| 6 | 60 | 1.69 | 0.48 | 3.68 | 16d |
| 7 | 90 | 1.56 | 0.57 | 2.83 | 16e |

Alternatively, prior to forming apertures in the film, the molecular orientation can be modified by plastically deforming the film to optimize the relative angle between the orientation of the teeth and the molecular orientation of the film. For instance, the molecular orientation of an MD oriented film can be modified by plastically deforming the web in the CD resulting in a higher proportion of long chain molecules arranged in the CD. Preferably, the MD oriented film can be plastically deformed such that the predominant molecular orientation is changed from the MD to the CD. The modified web can then pass through the nip formed by MD oriented teeth producing oval shaped apertures having reduced aspect ratios.

In order to modify the molecular orientation of the precursor web, the web can be stretched or prestrained to plastically deform the web prior to passing through the forming apparatus 100 shown in FIG. 1. In one embodiment, the precursor web can be stretched to plastically deform the web by incremental stretching. As used herein, the term, "incremental stretching", also referred to as ring rolling, is a process in which a web is supported at closely spaced apart locations and then the unsupported segments of the web between these closely spaced apart locations are stretched. This can be accomplished by passing the web through a nip formed between a pair of meshing corrugated rolls, which have an axis of rotation perpendicular to the direction of web travel. Incremental stretching rolls designed for machine direction and cross direction stretching are described in U.S. Pat. No. 4,223,059.

Figure 17:
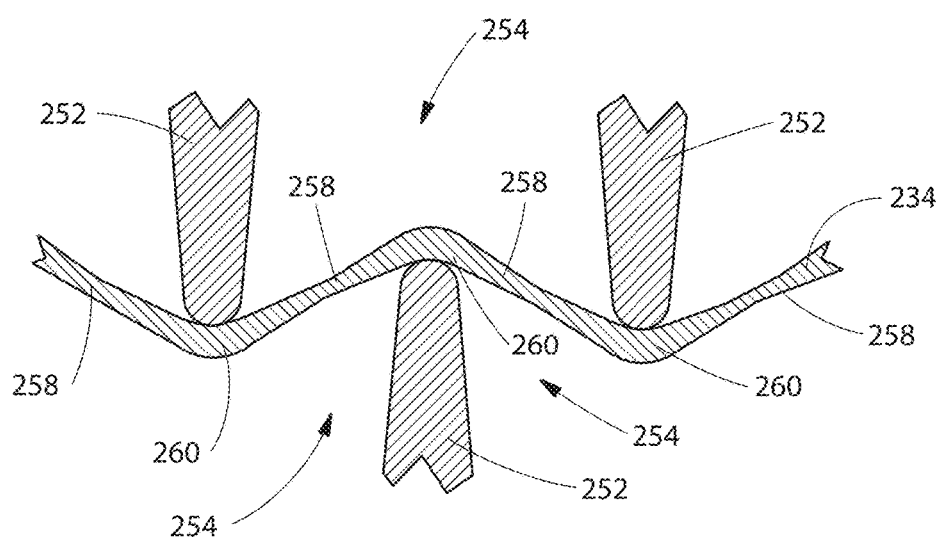
FIG. 17 is a cross-sectional representation of a portion of an incremental stretching apparatus.

FIG. 17 is an enlarged, fragmentary, cross-sectional view showing the interengagement of teeth 252 and grooves 254 of respective opposing activation rolls in a nip which incrementally stretch a web 234 of material therebetween. As shown, a portion of a web 234, which can be nonwoven web, is received between the interengaged teeth and grooves. The interengagement of the teeth and grooves causes laterally spaced portions of web 234 to be pressed by teeth 252 into opposed grooves 254. In the course of passing between activation rolls, the forces of teeth 252 pressing web 234 into opposed grooves 254 impose within web 234 tensile stresses that act in the machine or cross machine direction depending on the orientation of the teeth and grooves on the rolls. The tensile stresses can cause intermediate web sections 258 that lie between and that span the spaces between the tips of adjacent teeth 252 to stretch or extend in a machine or cross machine direction, which can result in a localized reduction of the web thickness at each of intermediate web sections 258. For nonwoven webs, the stretching can cause fiber reorientation, a reduction in basis weight, and controlled fiber destruction in the intermediate web sections 258.

Although the portions of web 234 that lie between the adjacent teeth are locally stretched, the portions of the web that are in contact with the tips of the teeth may not undergo a similar degree of extension. Because of the frictional forces that exist between the surfaces at the rounded outer ends of teeth 252 and the adjacent areas 260 of web 234 that are in contact with the tooth surfaces at the outer ends of the teeth, sliding movement of those portions of the web surfaces relative to the tooth surfaces at the outer ends of the teeth is minimized Consequently, in some cases, the properties of the web 234 at those areas of the web that are in contact with the surfaces of the tooth tips change only slightly, as compared with the change in web properties that occur at intermediate web sections 258.

Some materials including polypropylenes, polyethylenes and polyesters are unable to with stand the high rate of strain involved with incremental stretching in commercial production. Such materials can be incrementally stretched at a low rate of strain according to the process apparatus described in U.S. Published Application No. 2008/0224351 A1. The publication describes a method and apparatus which uses activation members for incrementally stretching a web at a relatively low strain rate. The activation members include an activation belt and a single activation member wherein the activation belt and single activation member comprise a plurality of teeth and grooves that complement and engage one another at a depth of engagement in a deformation zone. The depth of engagement is capable of increasing linearly over the deformation zone. In exemplary embodiments the deformation zone can be controlled to increase linearly over at least a portion of the deformation zone such that a web interposed between the activation belt and the single activation member in the deformation zone is incrementally stretched at a low rate of strain.

Another type of stretching apparatus useful in the present invention is a tenter. Tenters have been used for transverse direction stretching in film stretching processes. A tenter apparatus has grips or clippers that grasp the film along the opposing edges of the film. The stretching occurs by divergence of the grips or clippers on opposing edges relative to the direction of longitudinal movement. Such apparatus is described in U.S. Pat. No. 3,816,584.

Other methods for plastically deforming the web include hydroforming and vacuum forming.

Subsequent to stretching, the web continues in the machine direction to nip 116 comprising a pair of counter-rotating, intermeshing rolls 102 and 104. The pair of intermeshing rolls 102 and 104 operates to form apertures in web 1. Intermeshing rolls 102 and 104 are more clearly shown in FIG. 2.

EXAMPLE 3

Film samples were tested for shrinkage according to ASTM method D2732-03. Square samples (4 inches on each side) were cut from 100 mesh film, immersed in 100° C. glycerol for 30 seconds, then removed and dimensions re-measured. Five specimens were tested for each material and the results averaged. Without any pre-straining, the 100 mesh film sample exhibited shrinkage in the machine direction but not in the cross direction, indicating that the material is primarily oriented in the machine direction. The film was prestrained by incrementally stretching the web in the cross direction. After incremental stretching, the 100 mesh samples exhibited additional shrinkage in the cross direction, indicating that molecular orientation had been introduced in the cross direction as well. The data in Table 1 demonstrates that the magnitude of the shrinkage (and therefore molecular orientation) in the cross direction increases with depth of engagement employed during the ring-rolling process.

TABLE 3

| Film | Average MD measurement after heat treatment | Average CD measurement after heat treatment |
| --- | --- | --- |
| 100 mesh | 3.86 | 4.13 |
| 100 mesh ring-rolled at 0.050 inch depth of engagement | 3.75 | 3.69 |
| 100 mesh ring-rolled at 0.070 inch depth of engagement | 3.64 | 3.13 |

EXAMPLE 4

A 100 mesh film was ring rolled prior to aperturing to illustrate the effects that prestraining the web has on apertures. 100 mesh film was apertured using 0.050 inch pitch intermeshing rolls online at a speed of 1300 feet per minute. Data shown below illustrates that ring-rolling of the films prior to aperturing leads to a decrease in the aspect ratio of the apertures, an increase in the size of the apertures and increase in the air permeability of the films. Photomicrographs of the apertures formed in samples 8 through 11 are shown in FIGS. 18a through 18d, respectively.

TABLE 4

Figure 18A:
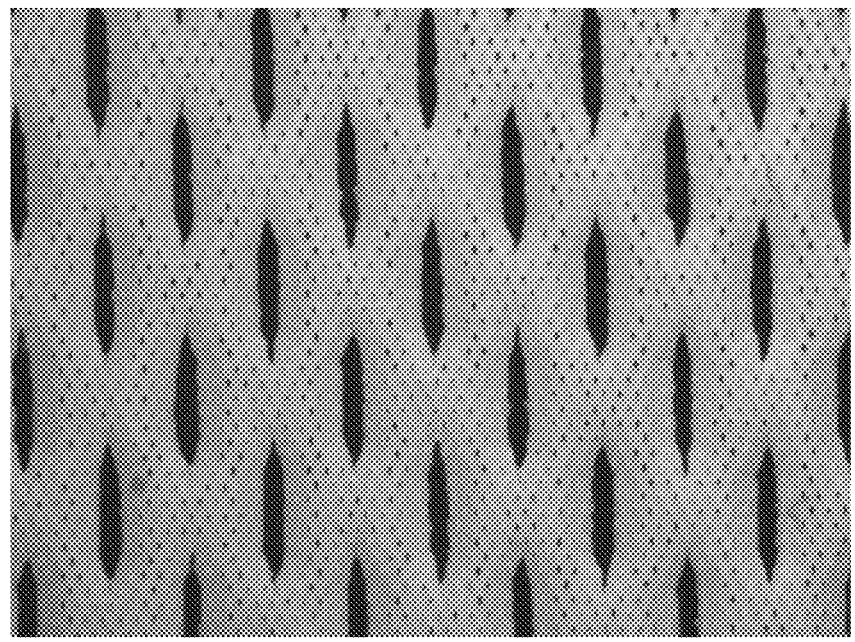
FIG. 18a through 18d are photomicrographs of the apertures formed in samples 8 through 11, respectively in Example 4.
Figure 18B:
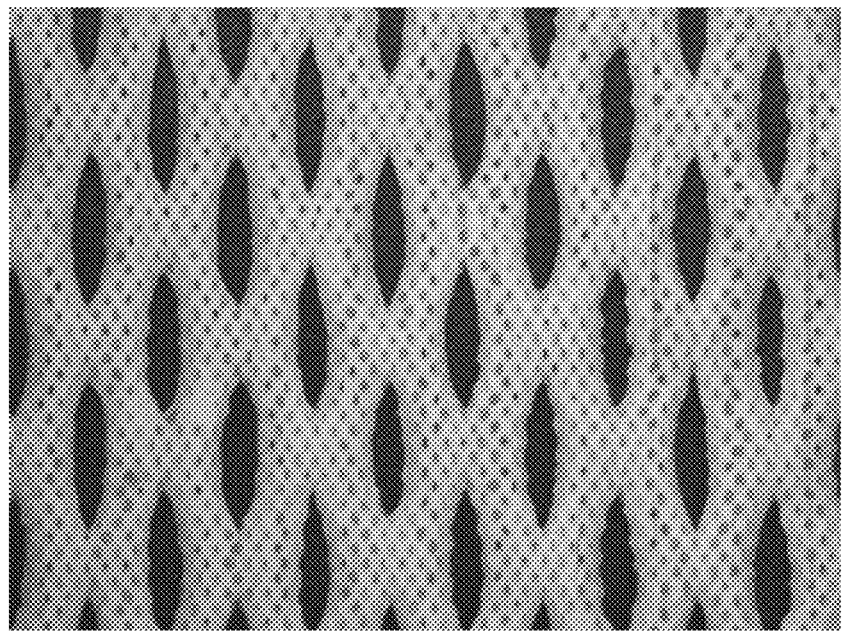
Figure 18C:
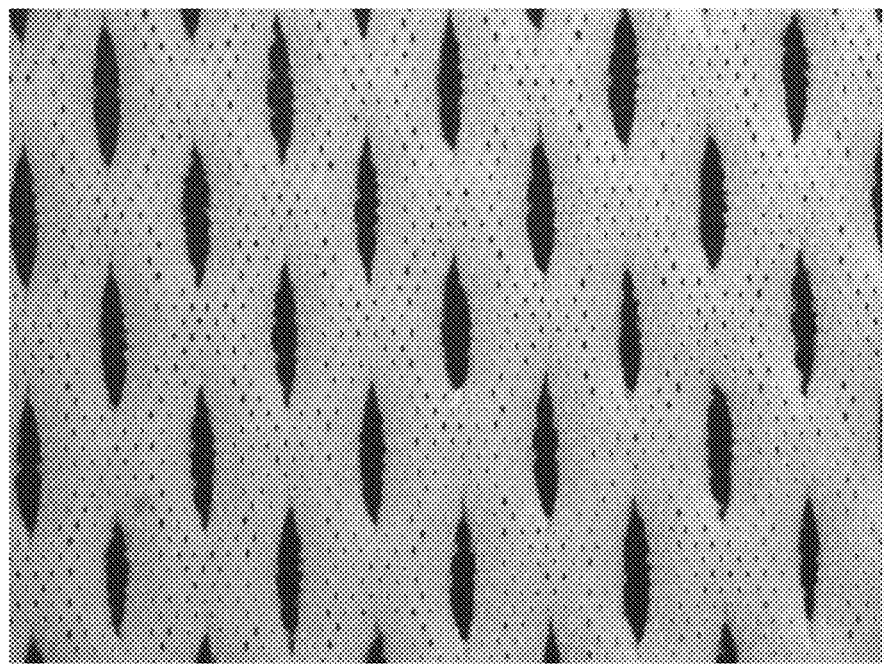
Figure 18D:
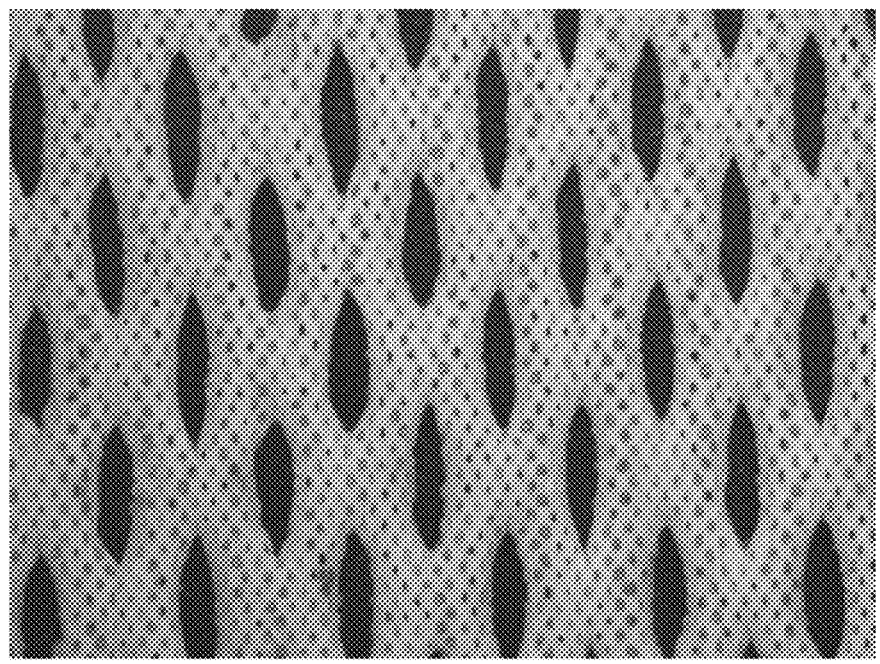

| FIGS. | FIG. 18a | FIG. 18b | FIG. 18c | FIG. 18d |
| --- | --- | --- | --- | --- |
| Sample | 8 | 9 | 10 | 11 |
| Ring-rolled? | no | yes | No | Yes |
| Ring-roll Pitch (inches) | — | 0.060 | — | 0.040 |
| Ring-roll Depth of Engagement (inches) | — | 0.050 | — | 0.045 |
| Forming apparatus Temp (° C.) | 105° C. | 105° C. | 94° C. | 94° C. |
| Average Aperture Length (mm) | 2.11 | 2.24 | 2.06 | 2.06 |
| Average Aperture Width (mm) | 0.33 | 0.54 | 0.37 | 0.55 |
| Average Aperture Aspect Ratio | 6.5 | 4.2 | 5.6 | 3.8 |
| Average Aperture Size (mm$^2$) | 0.8 | 0.9 | 0.7 | 0.8 |
| Air Permeability (cubic feet per minute) | 347 | 572 | 337 | 517 |

EXAMPLE 5

Figure 19A:
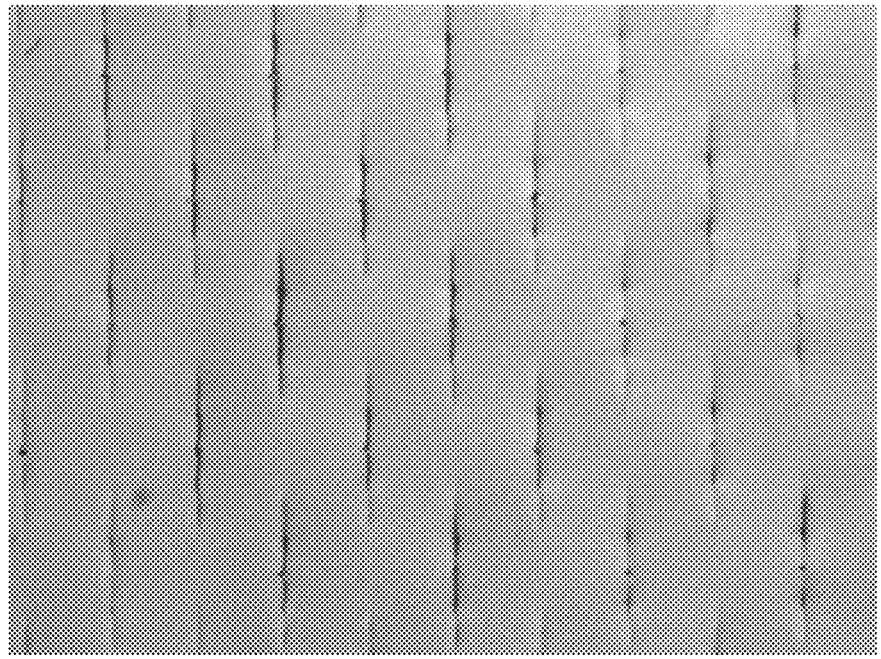
FIGS. 19a and 19b are photomicrographs of the apertures formed in samples 12 and 13, respectively in Example 5.
Figure 19B:
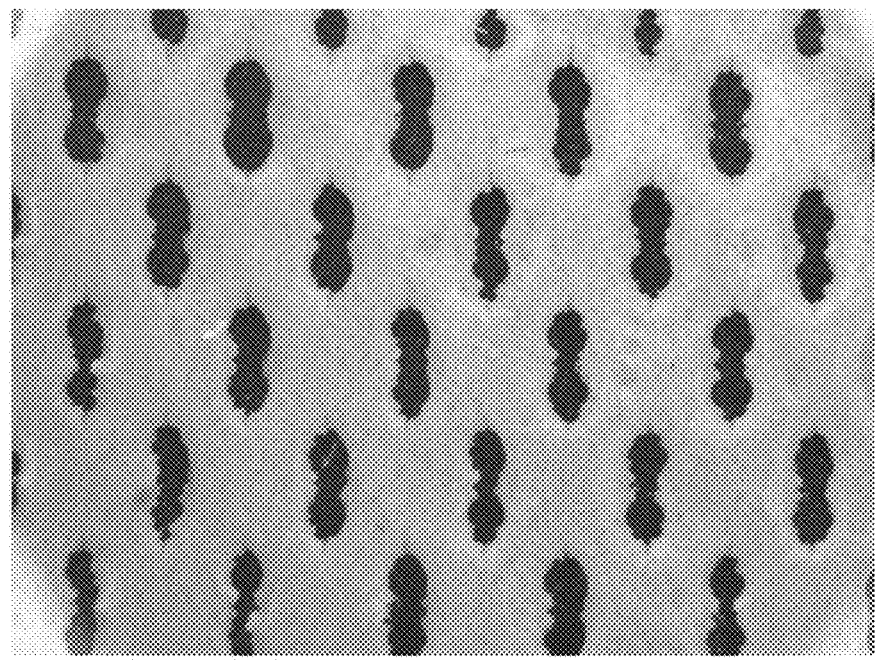

A flat film was apertured with and without pre-stretching the film. A flat film sample (TS3 Flat film obtained from Tredegar Film Products, Terra Haute, Ind.) was apertured using 0.050 inch pitch intermeshing plates on the high speed research press. The temperature of the aperture forming plate was set at 100° C. and the temperature of the mating ring-roll plate was set at 22° C. Process conditions were set up to mimic a web speed of 3.125 meters per second at a depth of engagement of 2.6 mm. The resultant film (Sample 12) had apertures that are barely open and look like slits, with an aspect ratio of 20. Another sample of the same film was stretched by hand 50% in the cross direction prior to aperturing under the same conditions on the high speed research press. The resultant film (Sample 13) had open apertures with an aspect ratio of 3.4. Photomicrographs of the apertures formed in samples 12 and 13 are shown in FIGS. 19a and 19b, respectively.

TABLE 5

| Sample | Average Aperture Length (mm) | Average Aperture Width (mm) | Average Aperture Aspect Ratio | FIG. |
| --- | --- | --- | --- | --- |
| 12 | 2.1 | 0.1 | 20 | 19a |
| 13 | 1.7 | 0.5 | 3.4 | 19b |

The precursor web can be prestrained in zones forming a web having strained and unstrained regions which is subsequently apertured resulting in different aperture sizes in the strained and unstrained zones. The strained and unstrained regions can be continuous or discontinuous and can run in both MD and the CD.

EXAMPLE 6

A 100 mesh film was incrementally stretched in zones to prior to aperturing to form zones of apertures where each zone had different aperture sizes. A sample of 100 mesh film was passed through a 0.040 inch pitch ring-roll with a width of 3 inches so that only the center portion was activated. Depth of engagement on the ring-roll was 0.045 inches. This film was then apertured using 0.050 inch pitch forming apparatus at 0.045 inch depth of engagement and 1300 feet per minute line speed. The temperature of the toothed roll was 94° C. and the temperature of the mating roll was 99° C. The resultant apertured film had a central zone with large apertures and side zones with smaller apertures.

Laminate

Although apertured web 1 is disclosed in the illustrated embodiments as a single layer web made from a single layer precursor web 20, it is not necessary that it be so. For example, a laminate or composite precursor web 20 having two or more layers or plies can be used. In general, the above description for apertured web 1 holds, recognizing that a web 1 formed from a laminate precursor web could be comprised of volcano like structures 8 wherein the sidewalls 9 comprise one or more of the precursor web materials. For example, if one of the materials of a composite precursor web has very low extensibility, teeth 110 may punch more or less cleanly through, such that it does not contribute material to the volcano like structure sidewalls 9. Therefore, a three-dimensional web made from a composite or laminate precursor web 20 may comprise volcano like side walls 9 on apertures 6 that comprise material from less than all the precursor web materials.

Figure 20A:
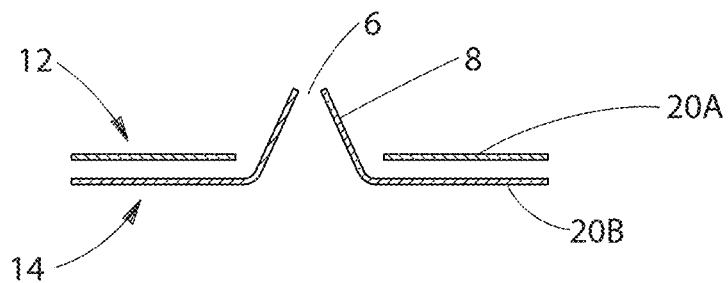
FIGS. 20A through 20C are schematic representations of various alternative laminate web configurations.
Figure 20B:
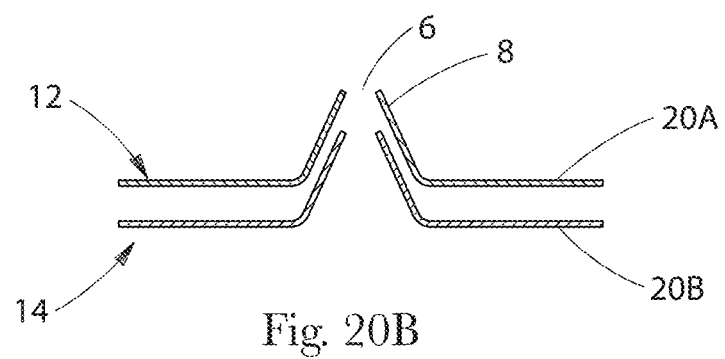
Figure 20C:
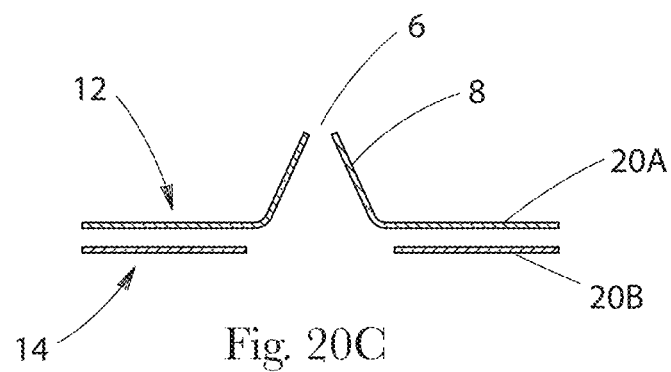

FIGS. 20A-20C show schematically various configurations of two layer composite webs 1 having a first surface 12 and a second surface 14, wherein extending from the second surface 12 are volcano-shaped structures 8. In general, two precursor webs designated as 20A and 20B can each be either a polymer film or a nonwoven web and processed together in layered relationship by the apparatus 150 or 200 as described above. Depending on the properties of each, such as ductility and extensibility, the result can be that either of precursor webs 20A or 20B can extend to form a three-dimensional volcano-like structure 8 as shown in FIGS. 19A and 19C. The other of precursor web 20A or 20B can simply be punched through to form a two-dimensional aperture, thereby not forming any substantially three-dimensional structure. However, as shown in FIG. 19B, both of precursor webs 20A or 20B can extend out of plane to form a three-dimensional volcano-like structure 8.

Multilayer apertured webs 1 made from composite laminate precursor webs 20 can have significant advantages over single layer apertured webs 1. For example, an aperture 6 from a multilayer apertured web 1 using two precursor webs, 20A and 20B, can comprise fibers (in the case of nonwoven webs) or stretched film (in the case of film webs) in a "nested" relationship that "locks" the two precursor webs together. One advantage of the locking configuration is that, while adhesives or thermal bonding may be present, the nesting allows forming a laminate web without the use or need of adhesives or additional thermal bonding between the layers. In other embodiments, multilayer webs can be chosen such that the fibers in a nonwoven web layer have greater extensibility than an adjacent film layer. Such webs can produce apertures 6 by pushing fibers from a nonwoven layer up and through an upper film layer which contributes little or no material to volcano-shaped structure 8 sidewalls 9.

In a multilayer apertured web 1 each precursor web can have different material properties, thereby providing apertured web 1 with beneficial properties. For example, apertured web 1 comprising two (or more) precursor webs, e.g., first and second precursor webs 20A and 20B can have beneficial fluid handling properties for use as a topsheet on a disposable absorbent article. For superior fluid handling on a disposable absorbent article, for example, second precursor web 20B can form an upper film layer (i.e., a body-contacting surface when used as a topsheet on a disposable absorbent article) and be comprised of relatively hydrophobic polymer. First precursor web 20A can be a nonwoven fibrous web and form a lower layer (i.e., disposed between the topsheet and an absorbent core when used on a disposable absorbent article) comprised of relatively hydrophilic fibers. Fluid deposited upon the upper, relatively hydrophobic layer can be quickly transported to the lower, relatively hydrophilic, layer. For some applications of disposable absorbent articles, the relative hydrophobicity of the layers could be reversed, or otherwise modified. In general, the material properties of the various layers of apertured web 1 can be changed or modified by means known in the art for optimizing the fluid handling properties of apertured web 1.

A distinct benefit of the apparatus 150 or 200 as described above for forming apertured webs for use in disposable absorbent articles is the ability to adapt and position the apparatus 150 or 200 as a unit operation in an existing process for making such articles. For example, apertured web 1 can be a topsheet in an absorbent article such as a sanitary napkin. Rather than make the apertured web off line, perhaps at a geographically remote location, apertured web 1 can be made on line by putting forming apparatus 150 in line with the supply of topsheet material on a production line for making sanitary napkins. Doing so provides several distinct advantages. First, having forming apparatus 150 making apertures in the topsheet directly on the sanitary napkin production line eliminates the need to purchase apertured webs, which can be costly when made by traditional processes, such as vacuum forming, or hydroforming. Second, forming apertures on the sanitary napkin production line minimizes the amount of compression and flattening that three-dimensional volcano-shaped regions are subject to. For example, when three-dimensional apertured formed film webs are produced and shipped on rolls, a significant amount of compression, as well as permanent compression set, of the formed film apertures takes place. Such compression is detrimental to the operation of the web as a fluid pervious topsheet. Third, toothed roll 104 can be configured such that toothed regions are made in predetermined patterns, so that the apertured portion of an apertured topsheet is formed in a predetermined pattern. For example, a topsheet can be made on line in which the apertures are only disposed in the middle portion of a sanitary napkin. Likewise, apertures can be formed such that apertured regions are registered with other visible components, including channels, indicia, color signals, and the like.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making apertures in a web, the method comprising:
   a. providing a laminate or composite precursor web material having a machine direction and a cross machine direction, the laminate or composite precursor web having a predominant molecular orientation in the machine direction, the laminate or composite precursor web comprising a film layer and a nonwoven layer;
   b. plastically deforming the laminate or composite precursor web in a direction perpendicular to the machine direction;
   c. providing a forming apparatus; and
   d. moving the plastically deformed precursor web material through the forming apparatus, wherein the forming apparatus heats and stretches the web forming apertures therein.

2. The method of claim 1, wherein the forming apparatus comprises a first member and a second member, wherein the second member is heated.

3. The method of claim 2, wherein the second member is heated to a temperature of about 75 degrees C.

4. The method of claim 2, wherein the first member is heated to a temperature which is less than the temperature of the second member.

5. The method of claim 1, wherein the apertures formed in the laminate or composite precursor web have an aspect ratio of less than 3.0.

6. The method of claim 1, wherein the apertures formed in the laminate or composite precursor web have an aspect ratio of less than 2.0.

7. The method of claim 1, wherein the apertures formed in the laminate or composite precursor web have an average aperture size of greater than 0.7 square mm.

8. The method of claim 1, wherein the step of forming apertures creates volcano-shaped structures, and wherein a plurality of microscopic aberrations are disposed on an inner surface of the volcano-shaped structures, and wherein the apertures are disposed on a distal end of the volcano-shaped structures.

9. The method of claim 1, wherein there are at least 20 apertures per square cm.

10. The method of claim 1, wherein the laminate or composite precursor web comprises a film layer and a nonwoven layer.

11. The method of claim 10, wherein the film comprises a blend of low density polyethylene and linear low density polyethylene.

12. The method of claim 10, wherein the nonwoven layer comprises a spunbond nonwoven or a carded nonwoven.

13. The method of claim 12, wherein the nonwoven layer comprises a plurality of polypropylene fibers.

14. The method of claim 10, wherein the film layer comprises a surfactant.

15. The method of claim 1, wherein the apertures range in size from 0.7 square mm to 0.9 square mm.

16. The method of claim 1, wherein the web exhibits an air permeability of between 337 cfm to 572 cfm.

* * * * *